United States Patent [19]
Zuk, Jr.

[11] Patent Number: 6,156,199
[45] Date of Patent: Dec. 5, 2000

[54] CENTRIFUGAL FILTRATION APPARATUS

[76] Inventor: Peter Zuk, Jr., 258 Old Littleton Rd., Harvard, Mass. 01451

[21] Appl. No.: 09/132,358

[22] Filed: Aug. 11, 1998

Related U.S. Application Data

[60] Provisional application No. 60/055,318, Aug. 11, 1997.

[51] Int. Cl.$^7$ .......................... B01D 61/00; B01D 21/26

[52] U.S. Cl. .................. 210/321.84; 210/323.1; 210/360.1; 210/380.1; 210/477; 422/72; 422/101; 436/177

[58] Field of Search .............. 210/360.1, 380.1, 210/407, 515, 477, 518, 650, 321.84, 323.1; 494/36; 422/72, 101; 436/177

[56] References Cited

U.S. PATENT DOCUMENTS

| | | | |
|---|---|---|---|
| 4,632,761 | 12/1986 | Bowers et al. | 210/650 |
| 4,722,792 | 2/1988 | Miyagi et al. | 210/360.1 |
| 5,112,484 | 5/1992 | Zuk, Jr. | 210/247 |
| 5,490,927 | 2/1996 | Herczeg | 210/321.84 |
| 5,647,990 | 7/1997 | Vassarotti | 210/650 |

*Primary Examiner*—David A. Reifsnyder
*Attorney, Agent, or Firm*—Brian D. Voyce

[57] ABSTRACT

A filtration device for separating filtrate and concentrate from a solution that contains a dead stop feature. The dead stop volume is determined by the location of an outlet port. The apparatus includes a housing with a means for collecting filtrate and a filter unit insertable within the housing. The filter unit contains a semipermeable membrane thereon for separating filtrate from concentrate.

63 Claims, 30 Drawing Sheets

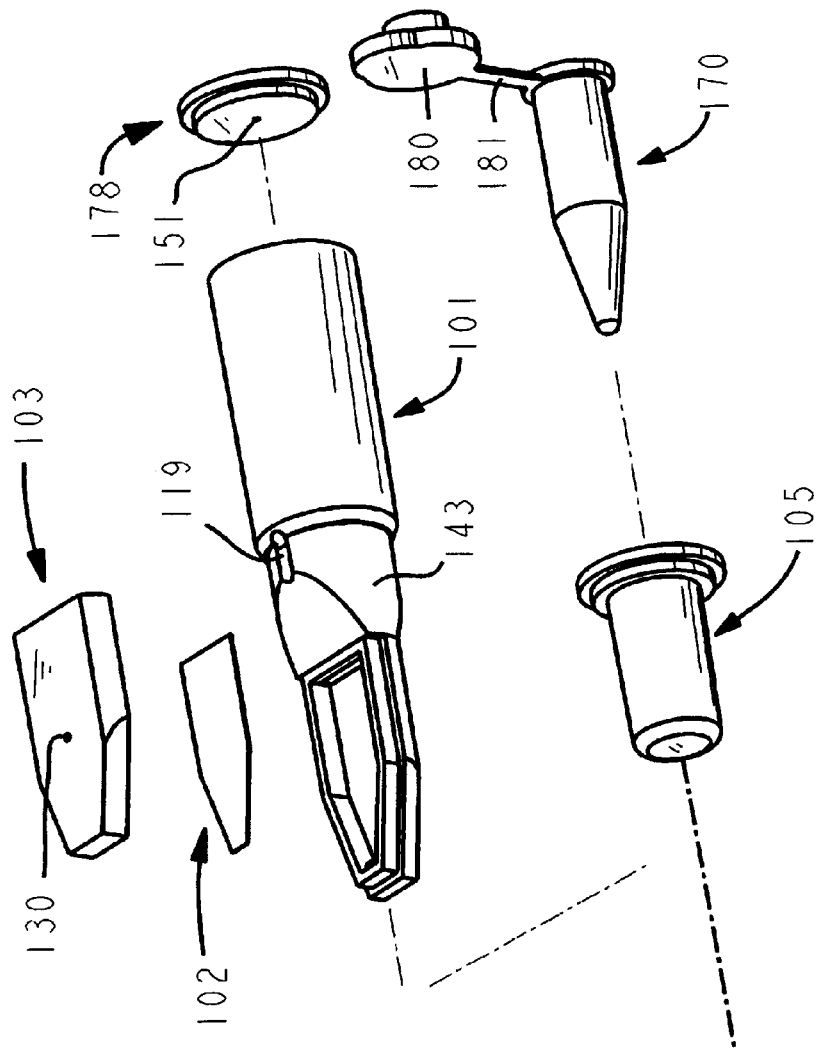
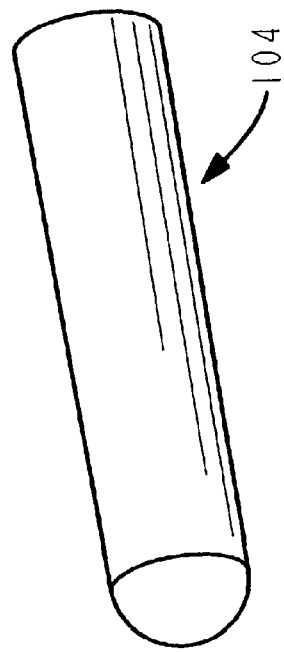
Fig. 1

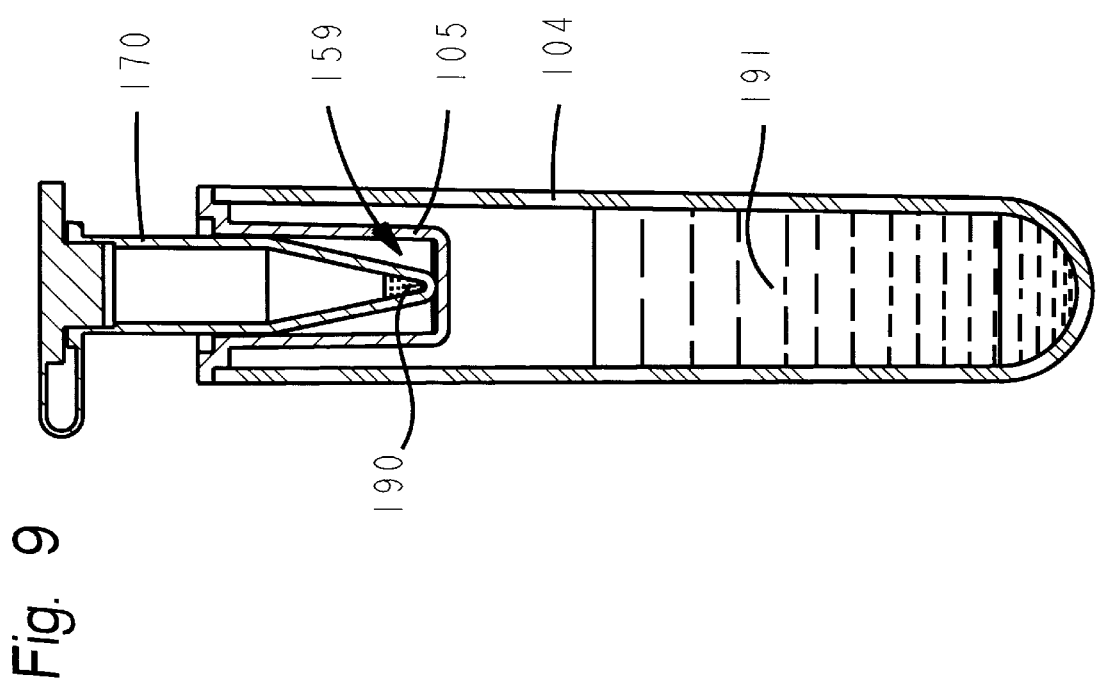

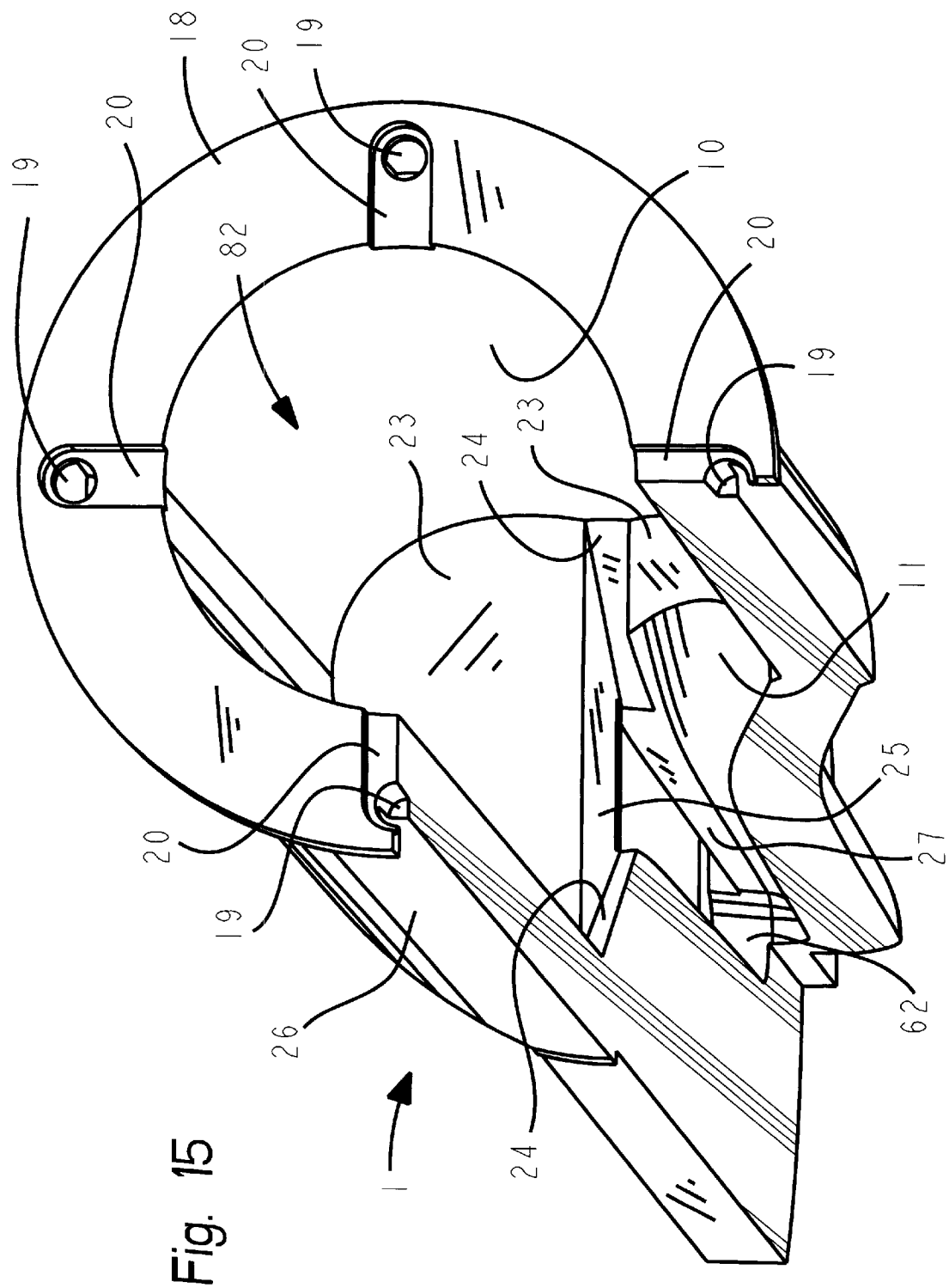

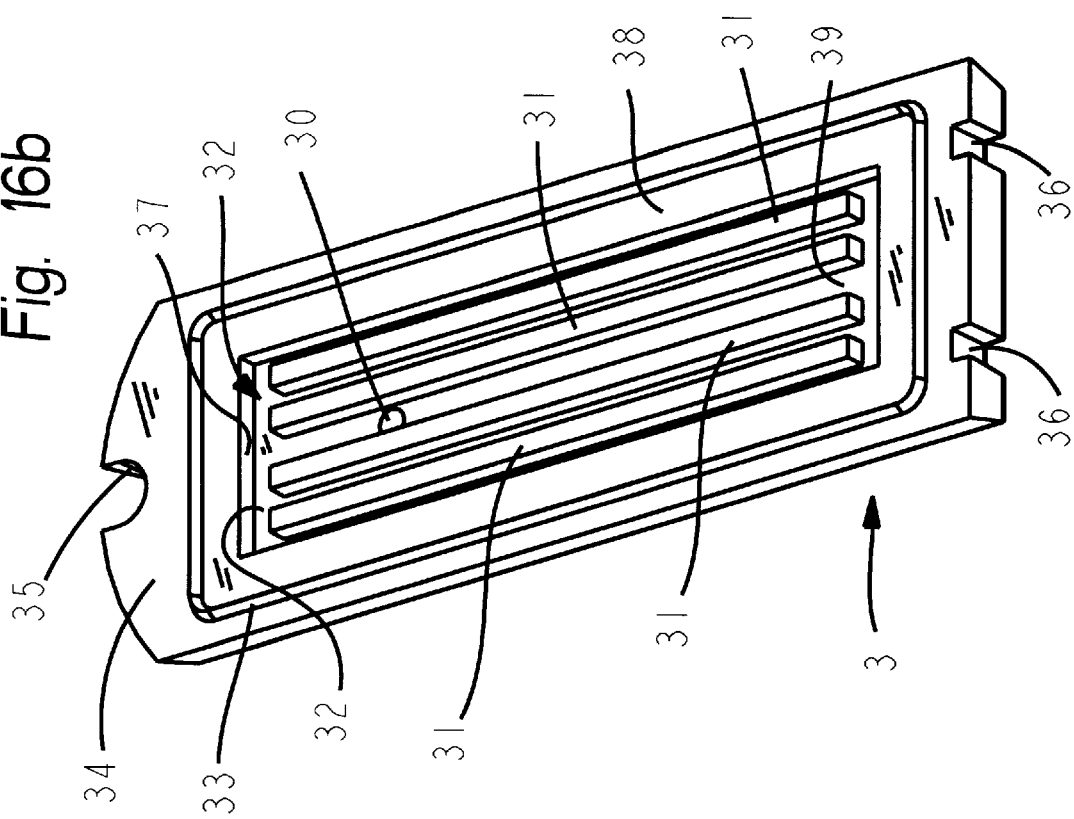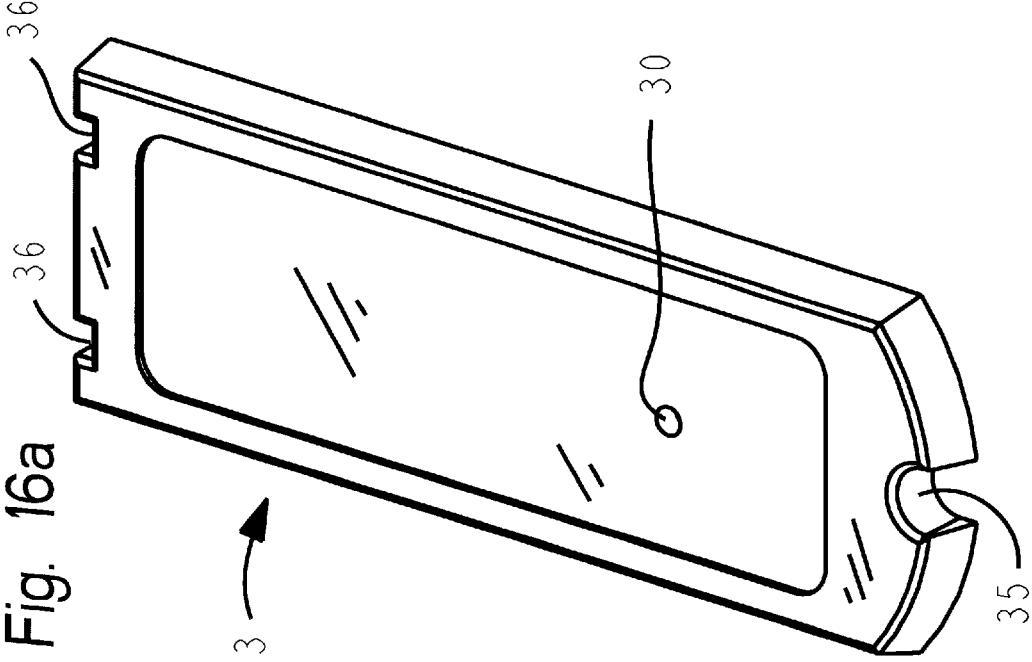

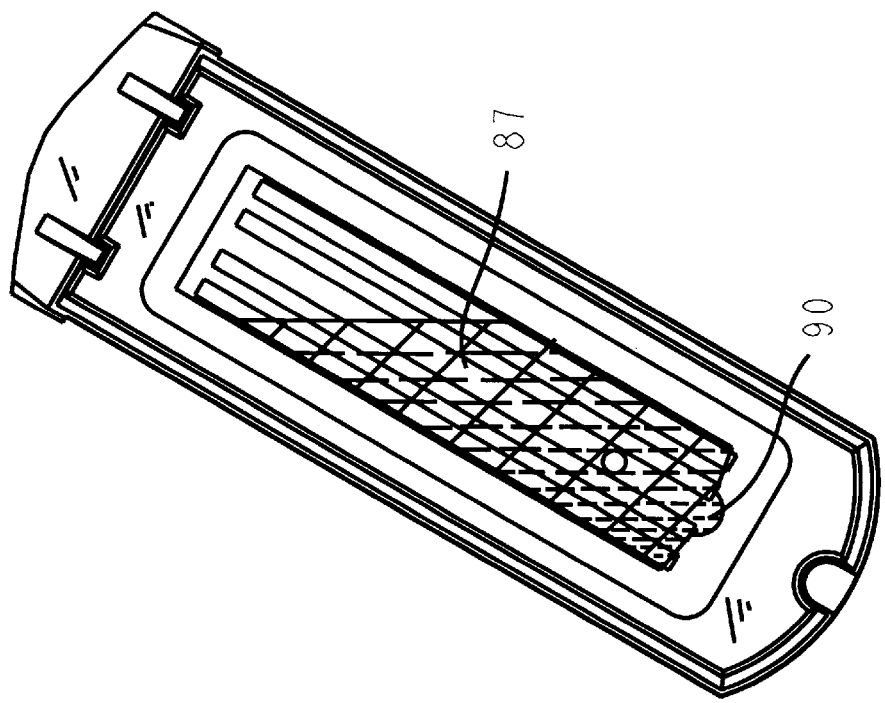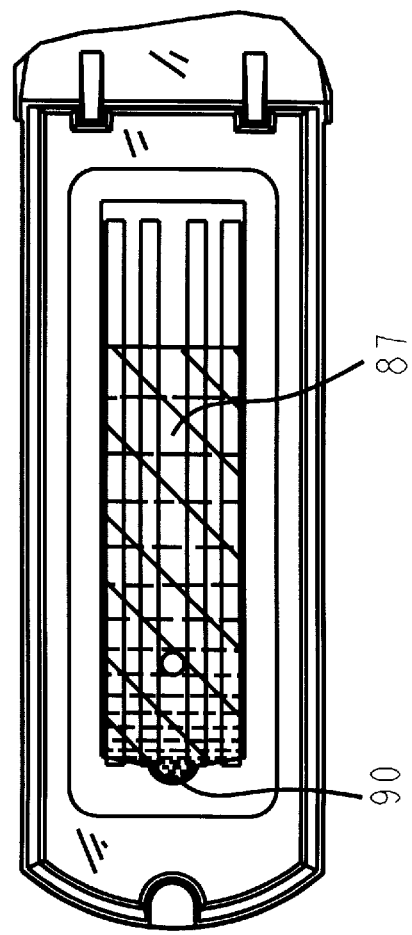

CENTRIFUGAL FILTRATION APPARATUS

CROSS REFERENCE TO RELATED APPLICATION

This application is a non-provisional of U.S. Provisional Patent Application Ser. No. 60/055,318 filed on Aug. 11, 1997.

BACKGROUND OF THE INVENTION

This invention relates to the filtration field, and more particularly, to an improved centrifugal filtration apparatus for filtering and concentrating a solution.

It is well known that the filtration of fluids may be accomplished through the use of filtration devices which utilize microporous filters to filter and concentrate a macromolecular solution. This technique has been utilized in centrifugal filtration apparatuses which rely on centrifugal forces to create pressure in the apparatus to force solutions through a filter which separates liquid solutions into filtrate and concentrate.

There are certain drawbacks, however, associated with conventional centrifugal filtration apparatus. There are many apparatus designs which prevent filtering to dryness. Some of these apparatus will filter to dryness when used in a swinging bucket centrifuge. Other apparatus allow filtration in both a fixed angle centrifuge and a swinging bucket centrifuge without filtering to dryness. These apparatus will however, retain a different amount of concentrate when used in a fixed angle centrifuge than they will when used in a swinging bucket centrifuge. These apparatus will also retain a different amount of concentrate when used in fixed angle centrifuges with different fixed angles.

Some of the conventional centrifugal filtration apparatus require a second spin to remove the retained concentrate (i.e. dead stop volume). In these apparatus it is difficult or impossible to remove the retained concentrate from the concentrate tube with a pipette.

Another problem with some of the conventional centrifugal filtration apparatus is that as the concentrate volume approaches its final retained volume, the active filter area approaches zero. Therefore, the filtration rate will slow dramatically as the concentrate volume approaches its final retained volume.

Another problem with the conventional centrifugal filtration apparatus is that they are open systems (i.e. they contain a venting means that vents to the atmosphere in the centrifuge).

Yet another problem with some of the conventional centrifugal filtration apparatus is that they are not scaleable (i.e. they are designed to be used as small volume centrifugal filters, or large volume centrifugal filters, not both).

Certain types of filtration devices, such as that disclosed in U.S. Pat. No. 4,632,761 to Bowers et al., are capable of preventing filtration to dryness and contain a dead stop feature which causes filtration to cease while there is concentrate remaining within the apparatus. This device, however, filters to dryness when spun at a 90° angle and therefore the dead stop feature will not work if the device is spun in a swinging bucket centrifuge. Also, in this type of filtration device, the amount of concentrate remaining after dead stop is dependent upon the angle of the centrifuge rotor. The filter surface area in this type of device is limited by the diameter of the device, and the surface area is relatively small when compared to the volume of liquid solution within the housing. Another problem with this type centrifugal filtration apparatus is that is an open system (i.e. it contains a venting means that vents to the atmosphere in the centrifuge). This type of filtration device is conductive to clogging because the heaviest and more dense molecules within the liquid solution are forced into the membrane filter. Accordingly, this device is limited because it will filter to dryness when spun in a swinging bucket centrifuge, it will filter to different dead stop volumes when used in fixed angle rotors with different angles, it is an open system and will vent potentially harmful gases to atmosphere during filtration, and its active filter surface area is limited by the diameter of the device.

The types of filtration devices disclosed in U.S. Pat. No. 4,722,792 to Miyagi et al. are capable of preventing filtration to dryness and contain a dead stop feature which causes filtration to cease while there is concentrate remaining within the apparatus. In this type of filtration device, the amount of concentrate remaining after dead stop is dependent upon the angle of the centrifuge rotor. Therefore, the dead stop volume will be different when the device is used in a swinging bucket rotor centrifuge than it will be when used in a fixed angle rotor, and will also be different when the device is used in fixed angle rotor centrifuges of different rotor angle. This means that the results obtained from this type of device when used in one type of centrifuge rotor can not be compared to the results obtained from this type of device when used in another type of centrifuge rotor. Another problem with this type centrifugal filtration apparatus is that is an open system (i.e. it must contain a venting means that vents to the atmosphere in the centrifuge). Another problem with this type of centrifugal filtration apparatus is that the filtration rate starts out high because of its relatively large filter surface area. However, as the concentrate volume approaches its dead stop volume, the active filter area approaches zero. Therefore, the filtration rate will slow dramatically as the concentrate volume approaches its final retained volume. Accordingly, this device is limited because it will filter to different dead stop volumes when used in centrifuge rotors with different angles, it is an open system and will vent potentially harmful gases to atmosphere during filtration, and the filtration rate will slow dramatically as the concentrate volume approaches the dead stop volume.

The types of filtration devices disclosed in U.S. Pat. No. 5,112,484 to Zuk et al. are capable of preventing filtration to dryness and contain a dead stop feature which causes filtration to cease while there is concentrate remaining within the apparatus. In this type of filtration device, the amount of concentrate remaining after dead stop is dependent upon the angle of the centrifuge rotor. Therefore, the dead stop volume will be different when the device is used in a swinging bucket rotor centrifuge than it will be when used in a fixed angle rotor, and will also be different when the device is used in fixed angle rotor centrifuges of different rotor angle. This means that the results obtained from this type of device when used in one type of centrifuge rotor can not be compared to the results obtained from this type of device when used in another type of centrifuge rotor. Another problem with this type centrifugal filtration apparatus is that is an open system (i.e. it must contain a venting means that vents to the atmosphere in the centrifuge). Another problem with this type of centrifugal filtration apparatus is that as the concentrate volume approaches its final retained volume, the active filter area approaches zero. Therefore, the filtration rate will slow dramatically as the concentrate volume approaches its final retained volume. Although the retained concentrate can be removed from this device with a pipette, the retained concentrate is best removed from this type of device using the concentrate cup with a second spin. This type of device is not well suited to filter small volumes. Accordingly, this device is limited because it will filter to different dead stop volumes when used in centrifuge rotors with different angles, it is an open system and will vent potentially harmful gases to atmosphere during filtration, the filtration rate will slow dramatically as the concentrate volume approaches the dead stop volume, it is not designed to filter small volumes, and it is not easy to remove the dead stop volume with a pipette.

The types of filtration devices disclosed in U.S. Pat. No. 5,490,927 to Herczeg et al. are capable of preventing filtration to dryness and contain a dead stop feature which causes filtration to cease while there is concentrate remaining within the apparatus. In this type of filtration device, the amount of concentrate remaining after dead stop is dependent upon the angle of the centrifuge rotor. Therefore, the dead stop volume will be different when the device is used in a swinging bucket rotor centrifuge than it will be when used in a fixed angle rotor, and will also be different when the device is used in fixed angle rotor centrifuges of different rotor angle. This means that the results obtained from this type of device when used in one type of centrifuge rotor can not be compared to the results obtained from this type of device when used in another type of centrifuge rotor. Another problem with this type centrifugal filtration apparatus is that is an open system (i.e. it must contain a venting means that vents to the atmosphere in the centrifuge). This type of device is not well suited to filter small volumes. This type of device utilizes the entire filter surface area until the dead stop volume is reached when used in a swinging bucket centrifuge. However when this type of device is used in a fixed angle rotor centrifuge the active filter area will approach zero as the concentrate volume approaches its final retained volume. Therefore, the filtration rate will slow dramatically as the concentrate volume approaches its final retained volume when used in a fixed angle centrifuge. This type of device requires a second spin to remove the retained concentrate solution. Accordingly, this device is limited because it will filter to different dead stop volumes when used in centrifuge rotors with different angles, it is an open system and will vent potentially harmful gases to atmosphere during filtration, the filtration rate will slow dramatically as the concentrate volume approaches the dead stop volume when used in a fixed angle rotor centrifuge, it is not designed to filter small volumes, and it requires a second spin to remove the retained concentrate solution.

It is therefore an object of the present invention to provide a filtration device which may be used in a swinging bucket centrifuge, as well as a fixed angle centrifuge, without filtering to dryness.

It is also an object of the present invention to provide a filtration device that will filter to approximately the same dead stop volume when used in either a swinging bucket rotor centrifuge, or when used in a fixed angle rotor centrifuge.

It is also an object of the present invention to provide a filtration device having a relatively high filtration membrane surface area thereby enabling filtration to occur at a higher rate.

It is also an object of the present invention to provide a filtration device that continues to use a relatively high filtration membrane surface area until the dead stop volume is attained, thereby enabling filtration to occur at a higher rate throughout the entire filtration process.

It is also an object of the present invention to provide a filtration device which minimizes the clogging of the semipermeable membrane thereby maximizing filter efficiency.

It is also an object of the present invention to provide a filtration device from which the retained concentrate solution can be easily removed with a pipette.

It is also an object of the present invention to provide a filtration device which can be used as a closed system (i.e. does not vent to atmosphere), or that can be used as an open system (i.e. vents to atmosphere).

It is a further object of the present invention to provide a filtration device which can be manufactured as a disposable small volume device, or as a disposable large volume device.

SUMMARY OF THE INVENTION

The foregoing problems of the prior art are solved, and the objects of the present invention are achieved, by use of a filtration apparatus constructed in accordance with the principles of the present invention.

In accordance with the present invention, the filtration apparatus for filtering and concentrating a solution includes a concentrate tube which is divided into two sections. The upper cylindrical section acts primarily as a reservoir for unfiltered solution and directs unfiltered solution from the upper section into the lower section of the concentrate tube. The upper section is shaped so that all of the solution in the upper section will flow into the lower section regardless of the centrifuge rotor angle. The lower section of the concentrate tube is mainly rectangular, but may be triangular shaped at the bottom. The volume of the lower section is made as small as possible to insure that the entire filter surface area is used to filter the maximum amount of solution. The lower section may contain a pipette tip channel to facilitate the removal of the retained concentrate with a pipette. The lower section is open on one side, or two sides. A micro-porous membrane or membranes may be sealed to the lower section so that the membrane covers the open side of the lower section of the concentrate tube, or so that the membranes covers the open sides of the lower section of the concentrate tube. Alternately the micro-porous membrane may be sealed to the filter cover, or covers. A second alternative is to seal the micro-porous membrane or membranes between the filter cover and a filter sealing gasket or gaskets. A filter cover is sealed to the open side of the lower portion of the concentrate tube, or two filter covers are sealed to the two open sides of the lower portion of the concentrate tube. The filter cover or covers contain a filter support means such as filter support ribs. The filter cover or covers also contains a filtrate outlet port. The position of the filtrate outlet port or ports determines the retained concentrate volume. The concentrate tube may contain a port or ports to allow displaced filtrate air to flow into the upper part of the concentrate tube to replace the filtered solution that flows from the concentrate tube into the filtrate tube.

The means for collecting the filtrate may include a filtrate tube. The concentrate tube may be sealed into the filtrate tube. The filtrate tube cap may contain a means to nest the concentrate storage tube.

BRIEF DESCRIPTION OF THE DRAWINGS

These and other objects, features and advantages of the invention will be evident from the following detailed description when read in conjunction with the accompanying drawings in which:

FIG. 1 is an exploded isometric view of the an embodiment of the filtration apparatus, constructed in accordance with the principles of the present invention, usable in a centrifuge;

FIG. 4 shows the fluid flow when the device is used in a swinging bucket centrifuge;

FIG. 9 is a cross-sectional view of the filtrate tube, filtrate cap, and concentrate storage tube, of the embodiment of the filtration device depicted in FIG. 1;

FIG. 10b is a partial top view of a transparent concentrate tube assembly of the embodiment of the filtration device depicted in FIG. 1, showing the concentrate, and active filter area in a 30° fixed angle rotor in;

FIG. 15 is an isometric view, having portions thereof removed, of the concentrate tube of the embodiment of the filtration device depicted in FIG. 11;

FIG. 16a is a top isometric view of the filter cover of the embodiment of the filtration device depicted in FIG. 11;

FIG. 16b is a bottom isometric view of the filter cover of the embodiment of the filtration device depicted in FIG. 11;

FIG. 23a is a partial top view of a transparent concentrate tube assembly of the embodiment of the filtration device depicted in FIG. 11, showing the usable filter surface area in a swinging bucket rotor;

FIG. 23b is a partial top view of a transparent concentrate tube assembly of the embodiment of the filtration device depicted in FIG. 11, showing the usable filter surface area in a 30° fixed angle rotor;

FIG. 24 shows the fluid flow when the device is used in a swinging bucket centrifuge;

DETAILED DESCRIPTION OF THE PREFERRED EMBODIMENTS

As referred to herein, the term upstream refers to a location of the flow of liquid prior to filtration through the filter element within the filtration device of the present invention. Conversely, the term downstream refers to a location of the flow of liquid after filtration through the filter element within the filtration device of the present invention. The term concentrate refers to the unfiltered liquid on the upstream side of the filter element. The term filtrate refers to the filtered liquid on the downstream side of the filter element. The terms retained volume or dead stop volume refer to the concentrate that remains on the upstream side of the filter element after filtration is complete. The term swinging bucket rotor refers to a centrifuge rotor that swings to an angle of 90° from the vertical (i.e. horizontal). The term active filter surface area refers to the filter surface area inside of the filter seal. The term usable filter surface area refers to the portion of active filter surface area actually being used at a particular time. The term axial orientation refers to the orientation relative to a central axis (i.e. the axial orientation of a cylinder is the radial orientation of the cylinder relative to an axis passing through the center of the cylinder).

Figure 4:
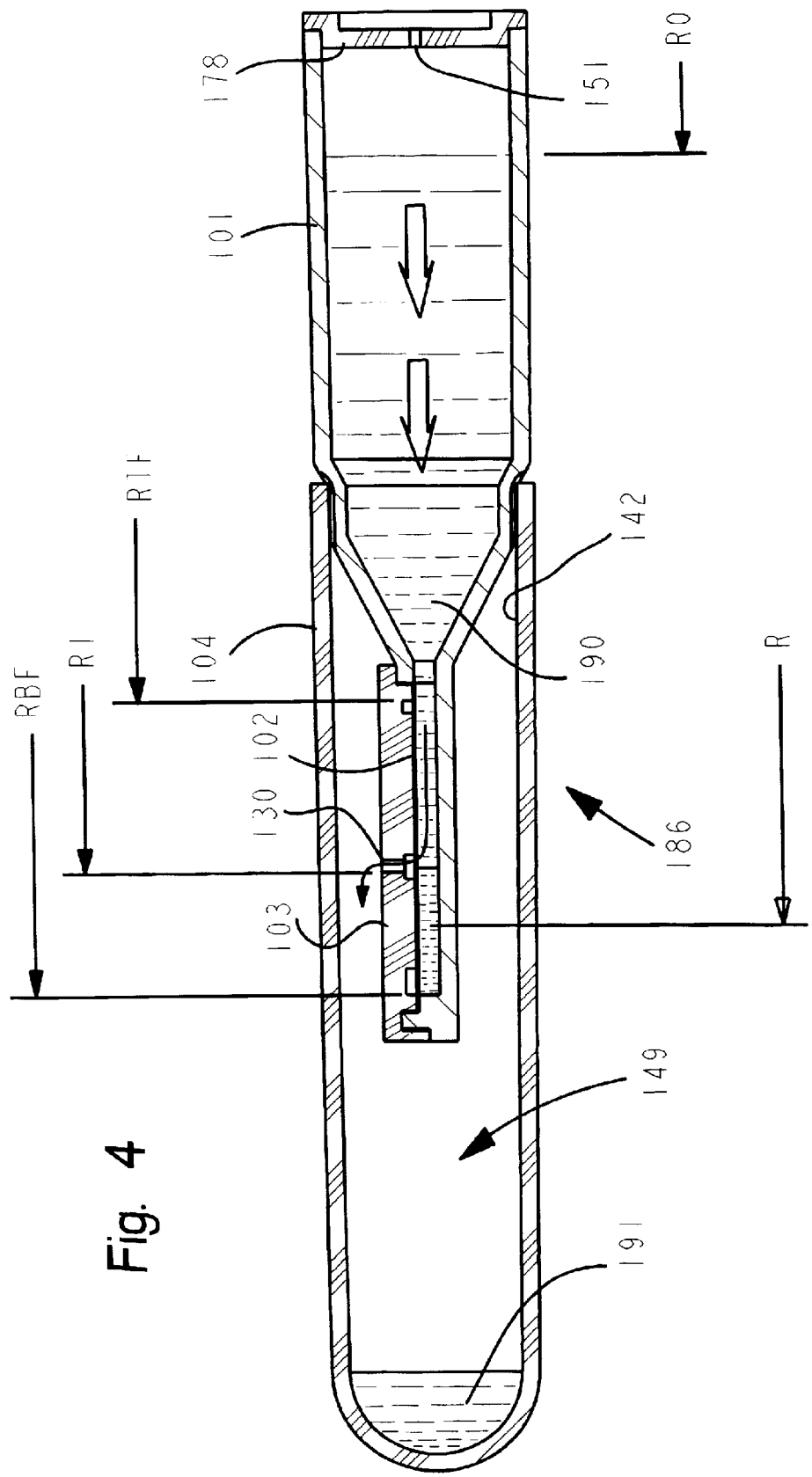
FIG. 4 is a cross-sectional view of the concentrate tube assembly with concentrate tube cap, and the filtrate tube of the embodiment of the filtration device depicted in FIG. 1.

Although various embodiments of the filtration device constructed in accordance with the present invention are disclosed herein, each embodiment enables the filtration device to keep the ratio of usable filter surface area to concentrate volume high throughout the filtration process. This can be best understood by referring to FIG. 4. The radii shown in FIG. 4 are defined as follows. R0 is the radius measured from the axis of rotation of the centrifuge to the top of the liquid on the upstream side of the device. RBF is the radius measured from the axis of rotation of the centrifuge to the bottom of the active filter surface area (i.e. the bottom of the wetted portion of the filter), and also the bottom of the liquid on both the upstream and downstream sides of the filter. RTF is the radius measured from the axis of rotation of the centrifuge to the top of the active filter surface area (i.e. the top of the wetted portion of the filter). R1 is the radius measured from the axis of rotation of the centrifuge to the bottom of the outlet port of the filter cover. R can have a value measured from the axis of rotation of the centrifuge that is greater in value than RBF and less in value than or equal to R0. In the pressure drop calculations that follow the variable $\rho$ refers to the liquid density, and the variable $\omega$ refers to the angular velocity of the centrifuge ($\omega=2\pi*$(rev/sec)).

Using the radii definitions defined in the previous paragraph the pressure drop across the filter can be calculated as follows.

First the pressure drop across the filter below the outlet port (i.e. RBF$\leq$R$\leq$R1) can be calculated as follows:

$$UPSTREAMPRESSURE = \int_{R0}^{R} \rho\omega^2 r\, dr = \frac{\rho\omega^2}{2}\{R^2 - R0^2\}$$

$$DOWNSTREAMPRESSURE = \int_{R1}^{R} \rho\omega^2 r\, dr = \frac{\rho\omega^2}{2}\{R^2 - R1^2\}$$

Therefore the pressure drop across the filter at any radius R below the outlet port is:

$$\Delta p = \frac{\rho\omega^2}{2}\{R1^2 - R0^2\}$$

Hence the region of the filter below the outlet port remains active until R0=R1 (i.e. the dead stop volume is reached).

Second the pressure drop across the filter above the outlet port (i.e. R1$\leq$R$\leq$RTF) can be calculated as follows:

$$UPSTREAMPRESSURE = \int_{R0}^{R} \rho\omega^2 r\, dr = \frac{\rho\omega^2}{2}\{R^2 - R0^2\}$$

For R1$\leq$R$\leq$RTF the downstream pressure is equal to zero.

From the above equations it can be seen that filtration will stop when R0=R1 (i.e. the dead stop volume is reached).

One embodiment of the filtration device constructed in accordance with the principles of the present invention, is shown in FIG. 1, FIG. 2, FIG. 3, FIG. 4, and FIG. 6. This embodiment includes the following major components: concentrate tube 101, filter element 102, filter cover 103, concentrate tube cap 178, filtrate tube 104, filtrate tube cap 105, and concentrate storage tube 170.

Figure 2:
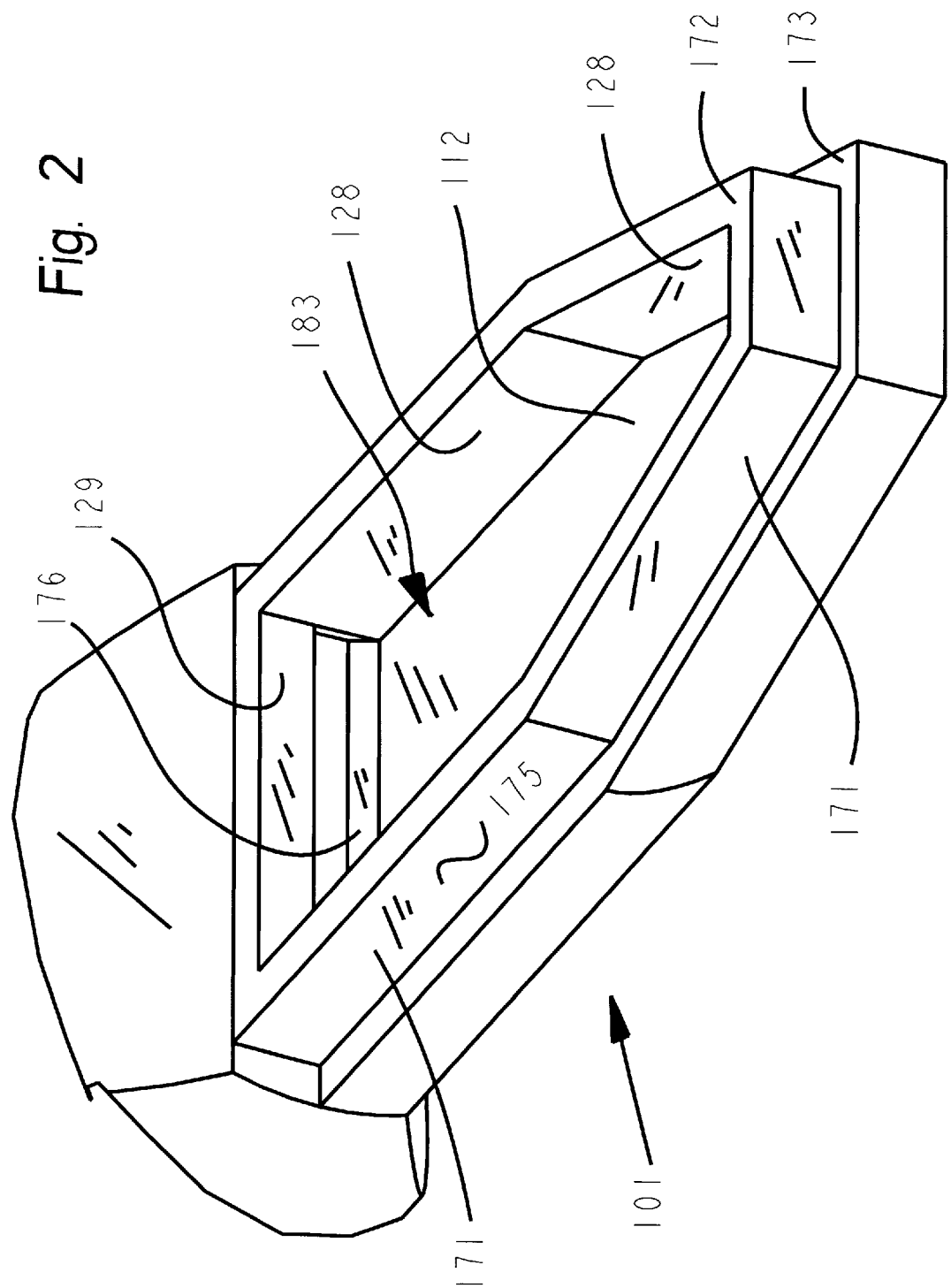
FIG. 2 is a partial isometric view of the lower section of the concentrate tube of an embodiment of the filtration device depicted in FIG. 1.
Figure 6:
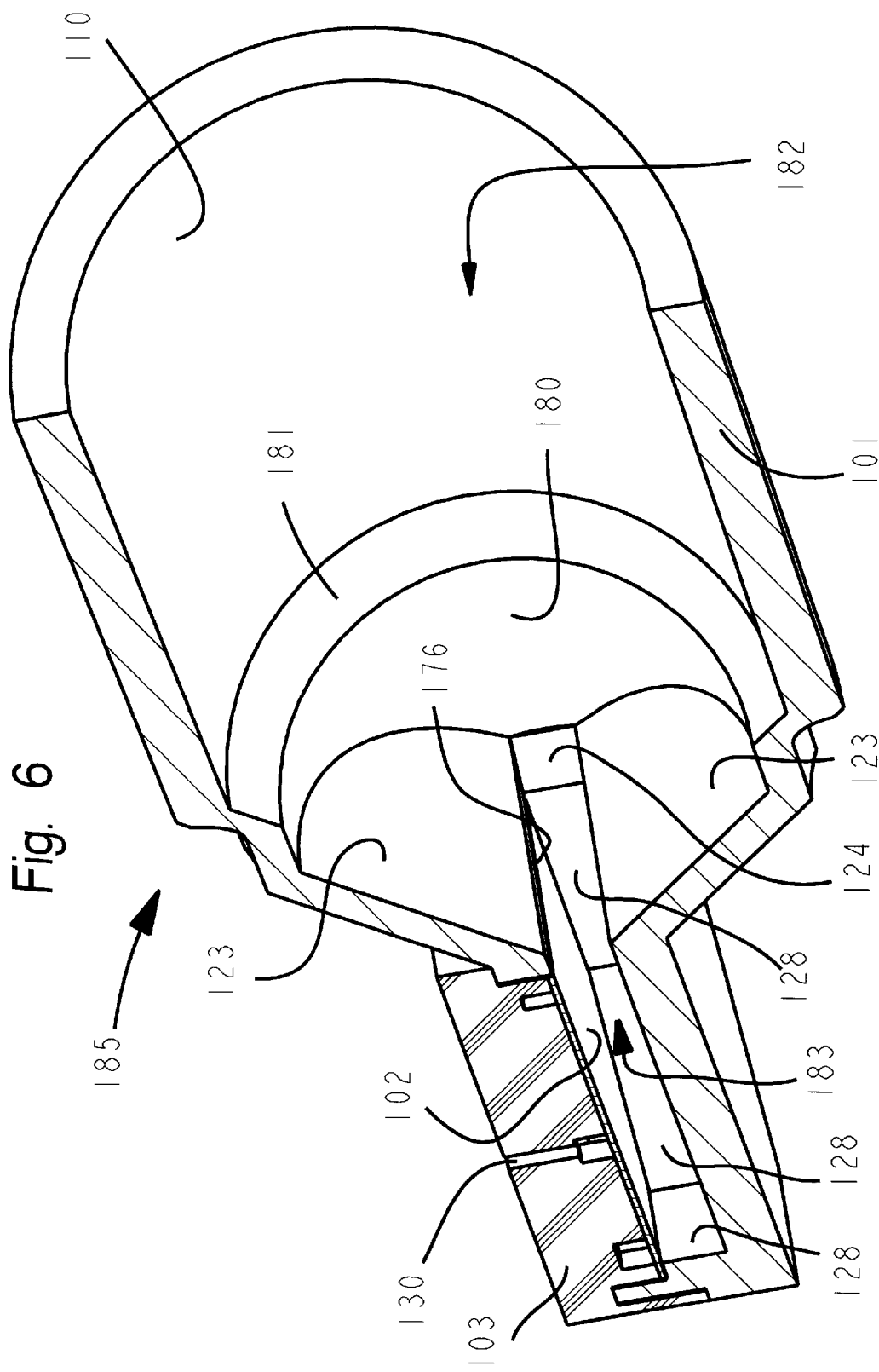
FIG. 6 is an isometric view, having portions thereof removed, of the concentrate tube assembly of the embodiment of the filtration device depicted in FIG. 1.

Referring to FIG. 1, FIG. 2, and FIG. 6 the concentrate tube assembly 185 contains concentrate tube 101, filter element 102, and filter cover 103. The concentrate tube assembly 185 contains a concentrate chamber which is divided into two parts, an upper concentrate chamber 182, and a lower concentrate chamber 183. The upper concentrate chamber 182 is formed by cylindrical wall 110, conical wall 181, cylindrical wall 180, front tapered walls 123, side tapered walls 124, and top and bottom walls 176. The lower concentrate chamber 183 is formed by side walls 128, bottom wall 112, back wall 129, and the upstream side of filter element 102. Conical wall 181, tapered walls 123, and tapered walls 124 assure that as filtration occurs all of the liquid in the upper concentrate chamber 182 will flow into lower concentrate chamber 183 when the apparatus is used at any rotor angle from 28° to 90°, regardless of the axial orientation of the apparatus in the centrifuge rotor.

Figure 3:
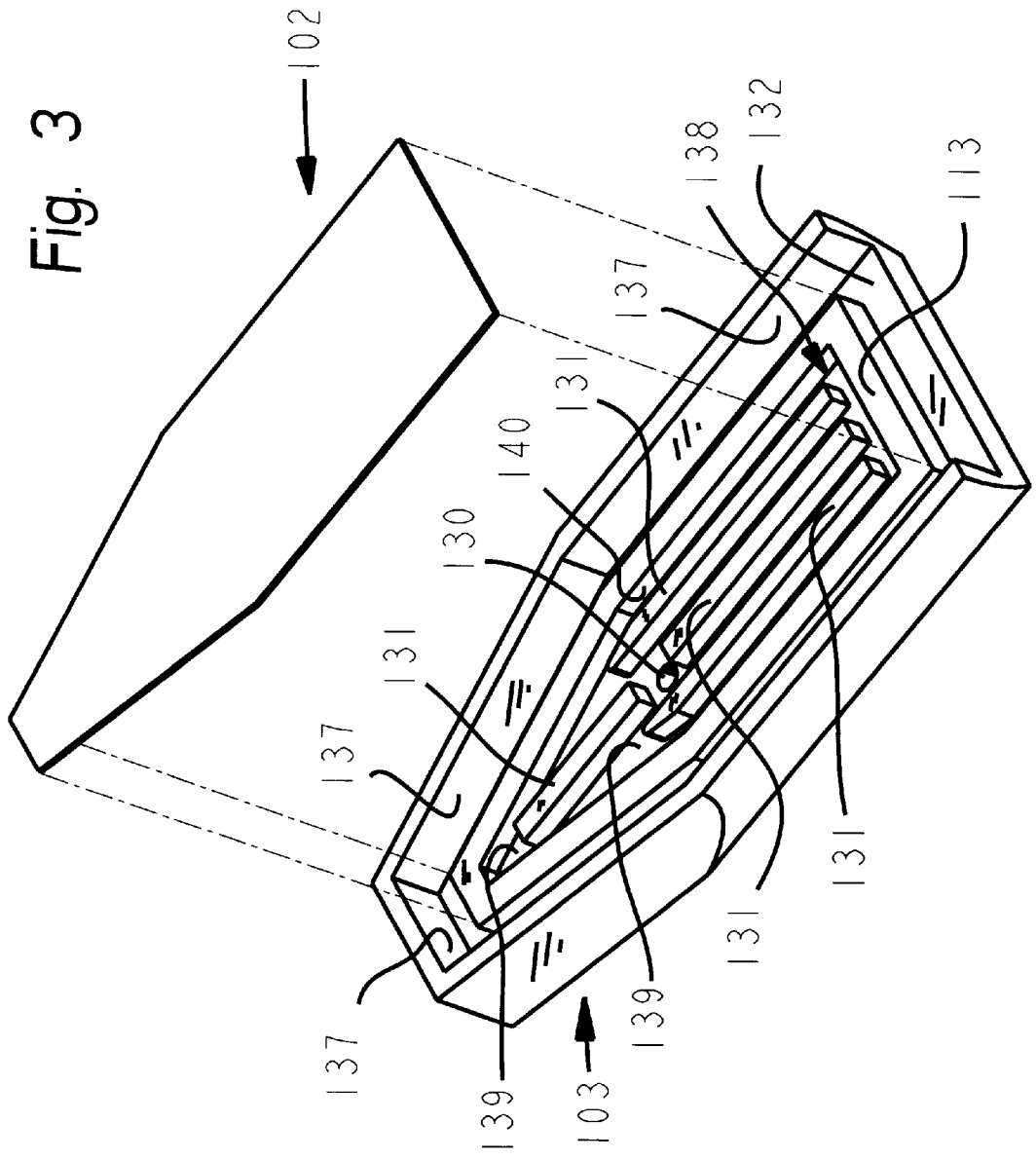
FIG. 3 is an exploded isometric view of the filter and filter cover of the embodiment of the filtration device depicted in FIG. 1.
Figure 7:
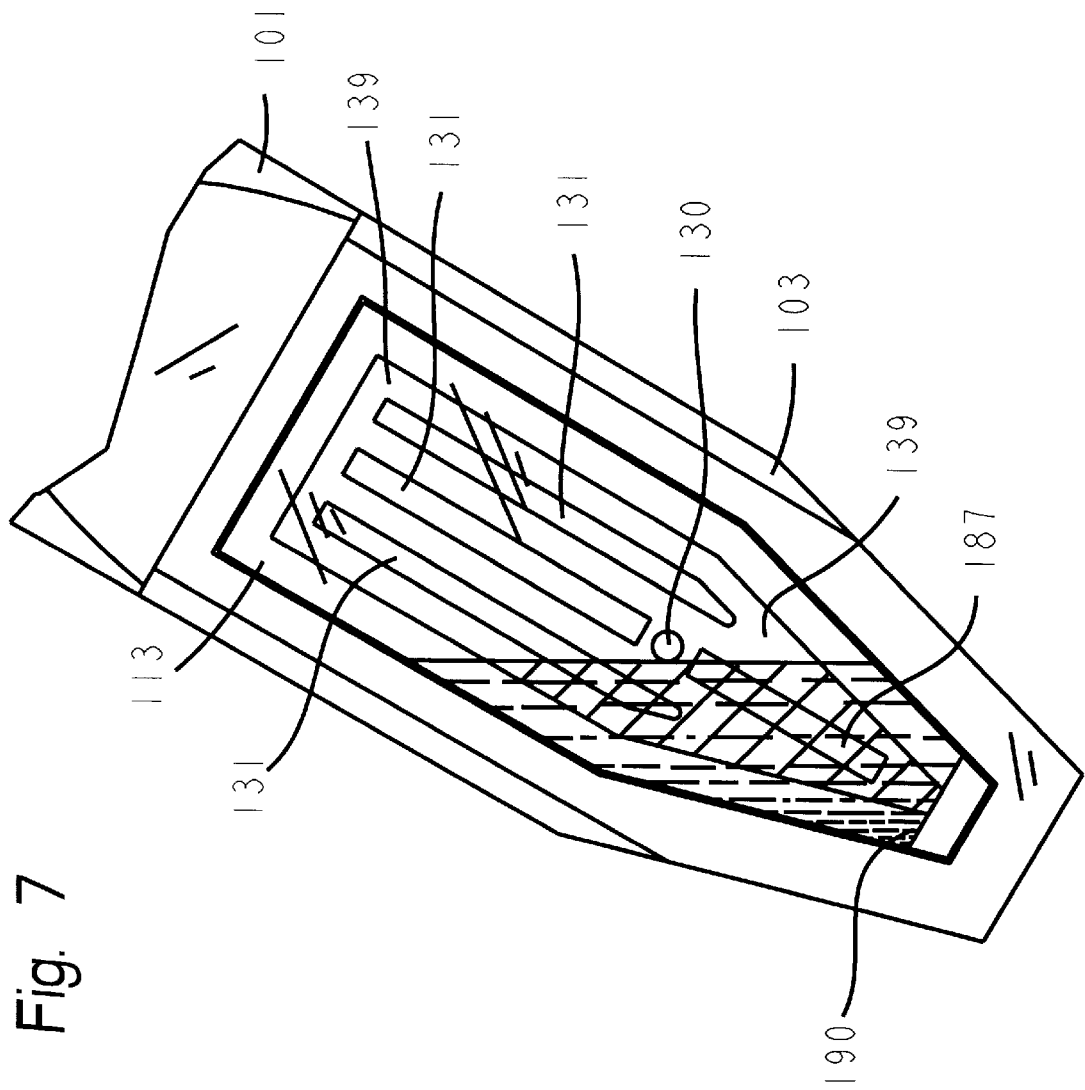
FIG. 7 is a partial top view of a transparent concentrate tube assembly of the embodiment of the filtration device depicted in FIG. 1, showing the retained concentrate in a 30° fixed angle rotor.
Figure 8:
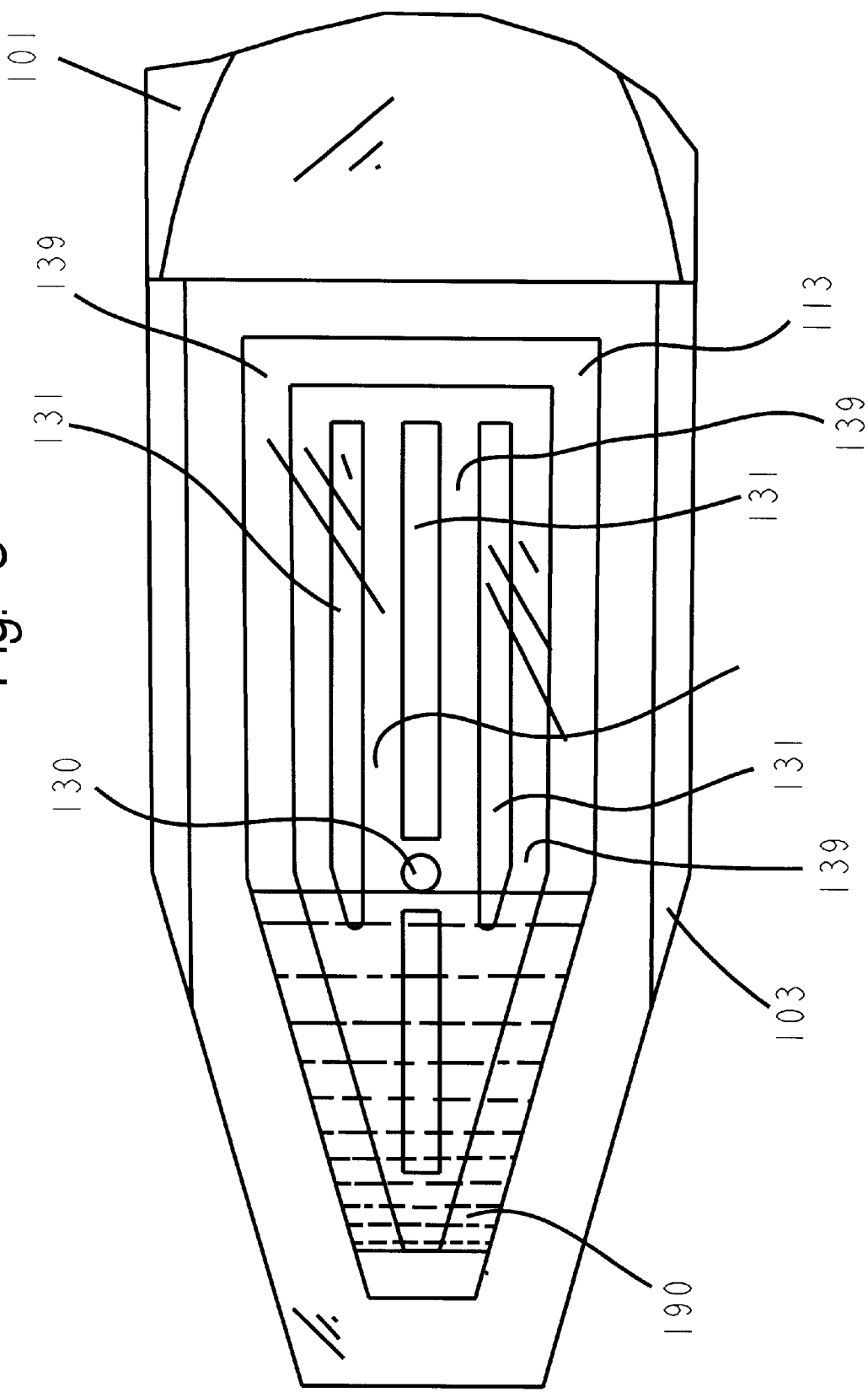
FIG. 8 is a partial top view of a transparent concentrate tube assembly of the embodiment of the filtration device depicted in FIG. 1, showing the retained concentrate in a swinging bucket rotor.

Referring to FIG. 3, FIG. 7, and FIG. 8 the outer periphery of filter element 102 is bonded to rib 113 of filter cover 103. The bond is preferably a heat seal, but could be a glue seal, a solvent bond or any other type of leak tight seal. Filter cover 103 contains filtrate chamber 138 which is formed by top inside surface 139 of filter cover 103, interior side walls 140 of rib 113 of filter cover 103 and the downstream side of filter element 102. Filter support ribs 131 protrude from top inside surface 139 of filter cover 103. Filter cover 103 also contains outlet port 130. As filtrate flows through filter element 102 into filtrate chamber 138, it collects in grooves 139 between filter support ribs 131, and grooves 139 between rib 113 and the filter support ribs 131. Filtrate flow from filtrate chamber 138 into outlet port 130 will be explained below.

Referring to FIG. 2, FIG. 3, FIG. 4, and FIG. 6, surface 132 of filter cover 103 is bonded to surface 172 of concentrate tube 101. The bond is preferably an ultrasonic weld, but could be a glue bond, a solvent bond, a heat bond, or any other type of leak tight bond. Outer walls 137 of filter cover 103 retain any weld flash.

The apparatus 186 is assembled, as shown in FIG. 1, FIG. 4, and FIG. 6 for filtration by inserting the concentrate tube assembly 185 into filtrate tube 104 so that outer surface 143 of the concentrate tube assembly 185 engages the inner surface 142 of filtrate tube 104 with an interference fit. The solution to be filtered or concentrated is then placed within the concentrate tube assembly. The solution fills the lower concentrate chamber 183 of concentrate tube assembly 185, and partially fills the upper concentrate chamber 182 of concentrate tube assembly 185. Concentrate tube cap 178 is then placed on the top of concentrate tube 101. The assembled device 186 is then inserted into an appropriate centrifuge rotor to perform the filtration. FIG. 4 shows the assembled device 186 oriented 90° from the vertical centrifuge axis (i.e. in the spinning swinging bucket rotor orientation).

Referring to FIG. 1, FIG. 3, and FIG. 4 the centrifugal force created by the spinning centrifuge rotor causes the lower molecular weight molecules of concentrate 190 on the upstream side of filter element 102 to flow through filter element 102, into filtrate chamber 138. Chamber 138 of concentrate tube assembly 185 is in fluid flow relationship with the interior of filtrate tube 104 via outlet port 130 of filter cover 103. Hence, filtrate that flows through filter element 102 into filtrate chamber 138 will accumulate in the bottom filtrate chamber 138, until the filtrate level in filtrate chamber 138 reaches outlet port 130 of filter cover 103. At this point any additional filtrate will flow from filtrate chamber 138 through outlet port 130 into the interior 149 of filtrate tube 104. Vent grooves 119 on concentrate tube 101 allow air in the interior of filtrate tube 104 to be vented into the centrifuge atmosphere, said air being displaced by filtrate 191 in the interior of filtrate tube 104. Vent grooves 119 on concentrate tube 101 prevent pressure buildup in filtrate tube 104 as filtrate tube 104 fills with filtrate. Vent hole 151 on concentrate tube cap 178 allows air to enter the interior of the concentrate tube assembly 185 to replace the filtered liquid, and thus prevent a vacuum buildup in the interior of concentrate tube assembly 185.

The filtration process continues until the liquid level on both the concentrate side of filter element 102, and the filtrate side of filter element 102 reach the outer most edge of outlet port 130 of filter cover 103. The outer most edge of outlet port 130 of filter cover 103 is the edge of outlet port that is the furthest from the axis of rotation of the centrifuge rotor. FIG. 8 shows this level for a swinging bucket centrifuge rotor, and FIG. 7 shows this level for a fixed angle rotor. Once the liquid reaches the level shown in FIG. 7 for a fixed angle rotor, or in FIG. 8 for a swinging bucket rotor, the pressure on the upstream side of filter element 102 will be the same as the pressure on the downstream side of filter element 102, thus liquid flow through filter element 102 will stop. The concentrate that remains on the upstream side of the filter element when filtration is complete is called the retained concentrate volume, or dead stop volume. When device 186 is used in a swinging bucket rotor the dead stop volume will be the same regardless of filter orientation. That is to say the dead stop volume will be the same if filtration device 186 is placed in the swinging bucket centrifuge rotor so that the filter element is oriented parallel to a vertical plane as shown in FIG. 8, or so that the filter element is oriented parallel to a horizontal plane as shown in FIG. 4, or so that the filter element is oriented at any angle relative to either the horizontal or vertical planes. The dead stop volume will be approximately the same for any centrifuge rotor angle from 20° to 90° when the filter element is oriented parallel to the vertical plane as shown in FIG. 7. For any axial orientation of the apparatus in a swinging bucket rotor the centrifugal force will force more dense molecules in the solution being filtered away from the upstream filter surface toward the dead stop region of lower concentrate chamber 183, thus keeping the filter element clean and maximizing the filter elements efficiency. When the apparatus is oriented in a fixed angle rotor as shown in FIG. 7 the centrifugal force will force the more dense molecules in the solution being filtered away from the upstream filter surface toward the dead stop region of lower concentrate chamber 183, thus keeping the filter element clean and maximizing the filter elements efficiency. When the apparatus is oriented in a fixed angle rotor 90° from the orientation shown in FIG. 7, so that the centrifugal force forces the more dense molecules away from the upstream side of the filter element the efficiency of the filter element will also be maximized. At all other axial orientations of the apparatus in a fixed angle rotor the filter elements efficiency will be reduced.

Figure 10B:
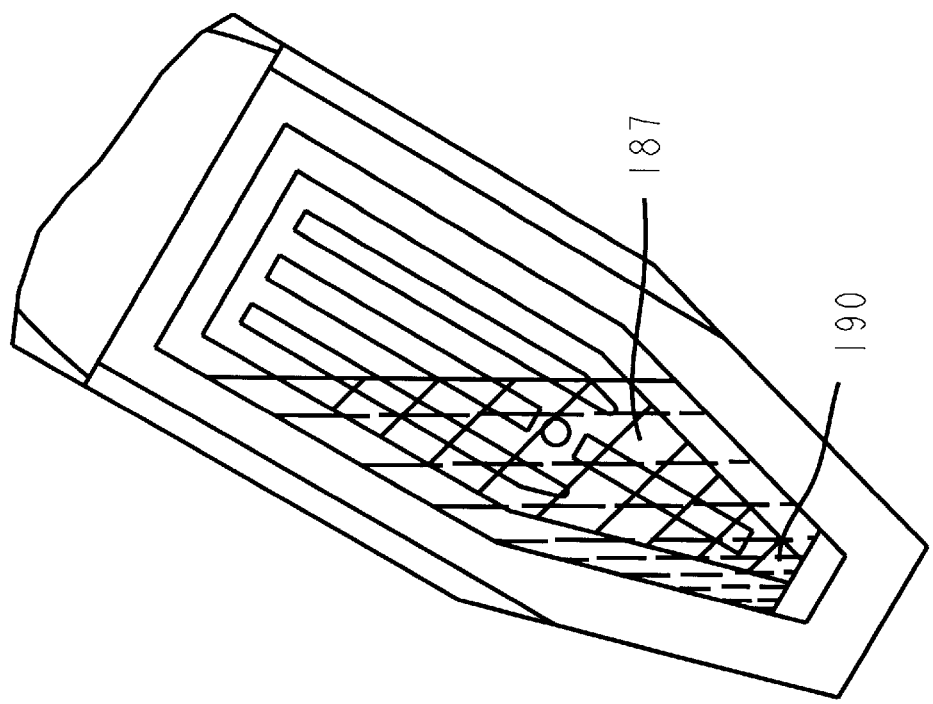
Figure 10A:
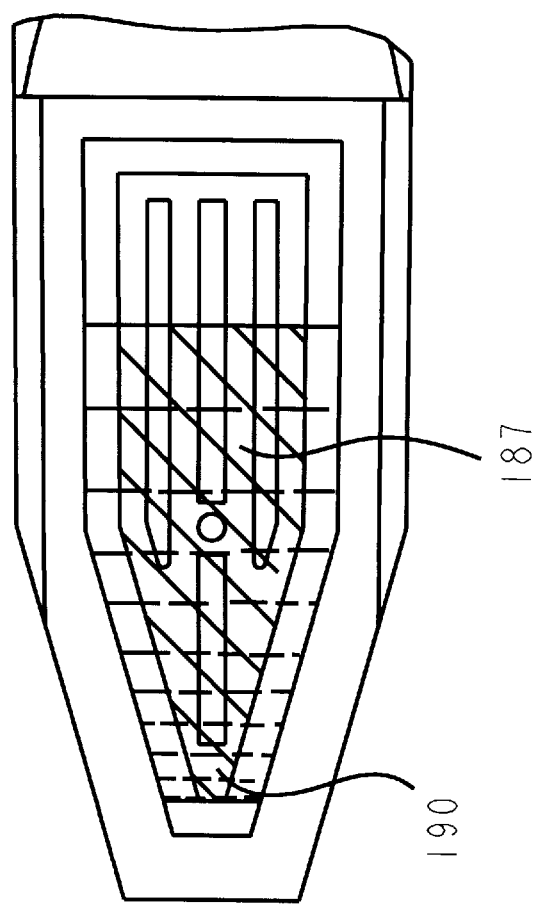
FIG. 10a is a partial top view of a transparent concentrate tube assembly of the embodiment of the filtration device depicted in FIG. 1, showing the concentrate, and active filter area in a swinging bucket rotor.

As long as the upstream side of the lower chamber 183 of concentrate tube assembly 185 is filled with liquid the entire active surface area of filter element 102 will be utilized. Referring to FIG. 10a and FIG. 10b, as the liquid level in lower chamber 183 of concentrate tube assembly 185 falls the portion 187 of the active surface area of filter element 102 that is wet by upstream liquid 190 becomes the usable filter surface area. A substantial portion 187 of the active filter surface continues to be usable filter surface area throughout the entire filtration process. For the embodiment shown in FIGS. 1 through 10b the ratio of (usable surface area)/(concentrate volume) increases throughout the filtration process. Throughout the entire filtration process none of the downstream active filter surface area is occluded.

Figure 5:
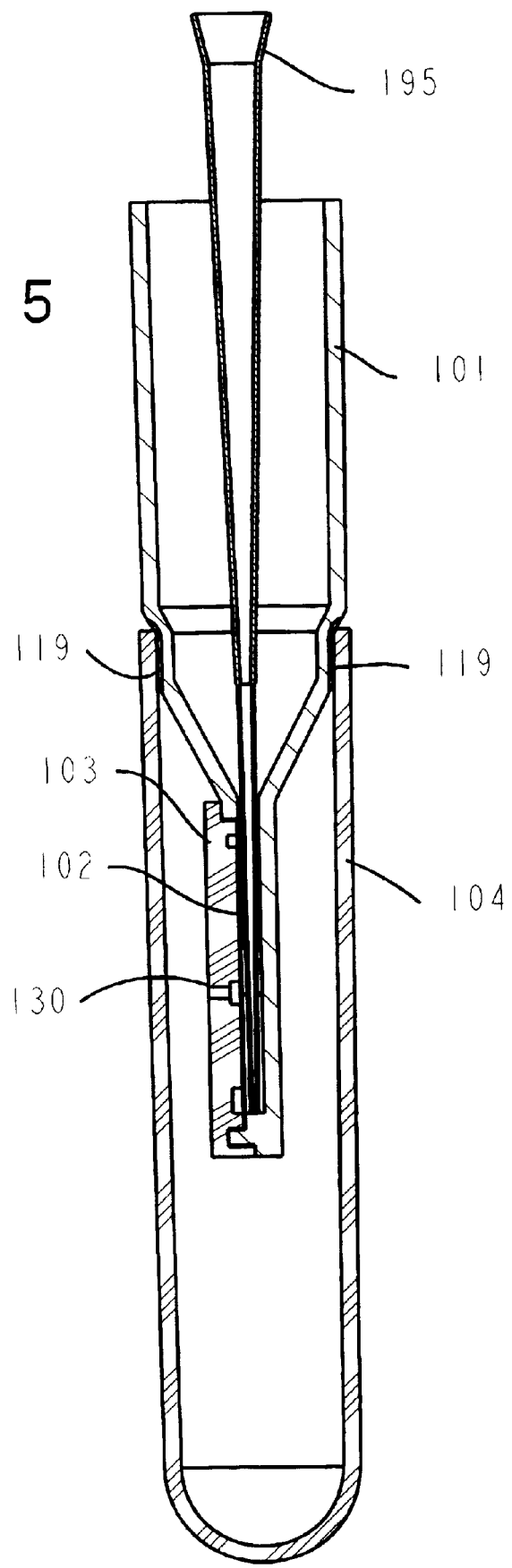
FIG. 5 is a cross-sectional view of the concentrate tube assembly, the filtrate tube, and a pipette tip, of the embodiment of the filtration device depicted in FIG. 1.

Referring to FIG. 5 and FIG. 9, when the filtration process is complete the user will remove the filtration device 186 from the centrifuge, and then remove the concentrate tube cap 178, and then remove the retained concentrate with the pipette tip 195 which will be attached to a pipette mechanism not shown. The retained concentrate can then be transferred from the pipette tip 195 to the concentrate storage tube 170. The concentrate tube assembly can then be removed from the filtrate tube 104 and discarded in a safe manner. The filtrate tube cap 105 can now be placed onto the filtrate tube. Filtrate tube cap 105 contains chamber 159 which is used to nest concentrate tube storage tube 170. This allows the concentrate sample and the filtrate sample to be conveniently stored together.

An second embodiment of the filtration device constructed in accordance with the principles of the present invention, is shown in FIG. 11, FIG. 12, FIG. 13, FIG. 14, and FIG. 15 FIG. 16a, FIG. 16b, and FIG. 17. This embodiment includes the following major components: concentrate tube 1, filter element 2, filter cover 3, filtrate tube 4, and filtrate tube cap 5.

Referring to FIG. 11, FIG. 12, and FIG. 13, FIG. 14, FIG. 15, and FIG. 22 the concentrate tube assembly 85 contains concentrate tube 1, filter element 2, and filter cover 3. The concentrate tube assembly 85 contains a concentrate chamber which is divided into two parts, an upper concentrate chamber 82, and a lower concentrate chamber 83. The upper concentrate chamber 82 is formed by cylindrical wall 10, front tapered walls 23, side tapered walls 24, and top and bottom walls 25. The lower concentrate chamber 83 is formed by side walls 28, bottom wall 12, back wall 29, the upper side walls of the pipette channel 27, the bottom pipette channel wall 11, the end pipette wall 62, and the upstream side of filter element 2. Tapered walls 23, and tapered walls 24 assure that as filtration occurs all of the liquid in the upper concentrate chamber 82 will flow into lower concentrate chamber 83 when the apparatus is used at any rotor angle from 28° to 90°, regardless of the axial orientation of the apparatus in the centrifuge rotor.

The outer periphery of filter element 2 is preferably bonded to surface 13 of concentrate tube 1. The filter element bond is preferably a heat seal, but could be a glue seal, a solvent bond or any other type of leak tight seal. The well formed by side walls 61 of concentrate tube 1 facilitates the placement of filter element 2 prior to sealing the filter to surface 13 of concentrate tube 1.

Referring to FIG. 16a, FIG. 16b, FIG. 20, and FIG. 21 the filter cover 3 contains a well 32 formed by inside top wall 39, and side walls 37. Filter support ribs 31 protrude from top surface 39. Grooves 45 are formed in-between and around filter support ribs 31 of filter cover 3 by the top surface 39 of filter cover 3 and the side walls of filter support ribs 31 of filter cover 3, and by the side walls 37 of well 32 of filter cover 3. Filter cover 3 can also contain energy director 33. Filter cover 3 also contains alignment grooves 35 and 36. Filter cover 3 also contains outlet port 30.

Figure 11:
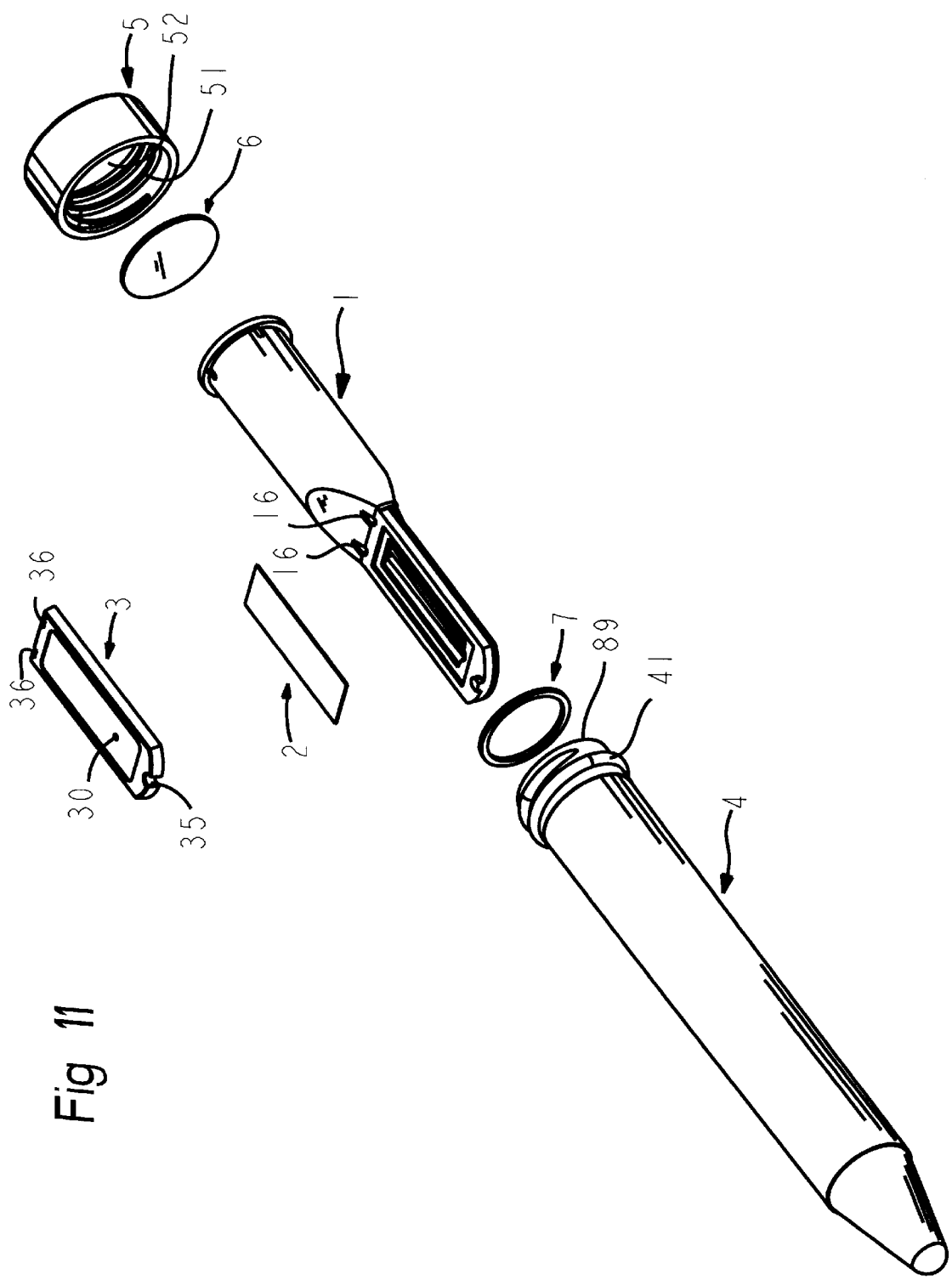
FIG. 11 is an exploded isometric view of the components of a second embodiment of a filtration apparatus, constructed in accordance with the principles of the present invention, usable within a centrifuge.
Figure 12:
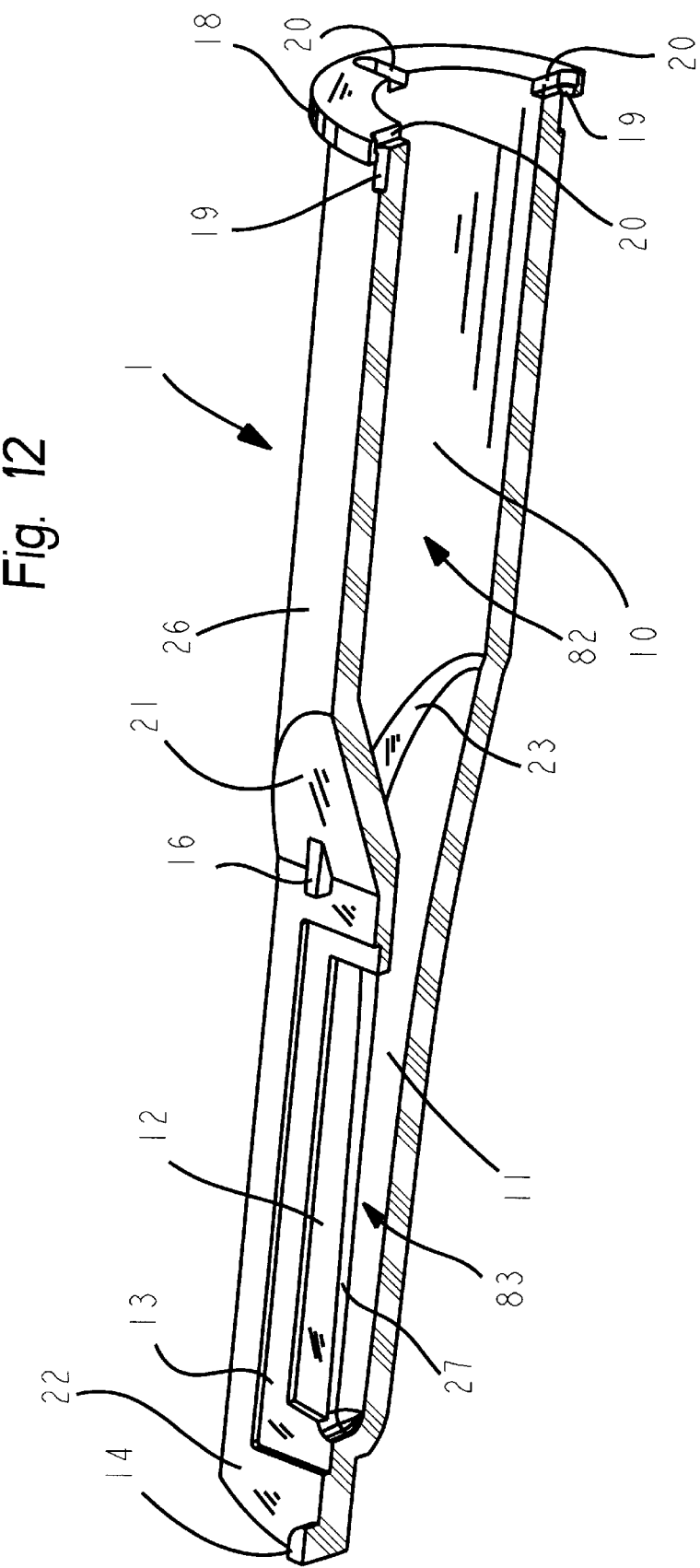
FIG. 12 is an isometric view, having portions thereof removed, of the concentrate tube of the embodiment of the filtration device depicted in FIG. 11.
Figure 17:
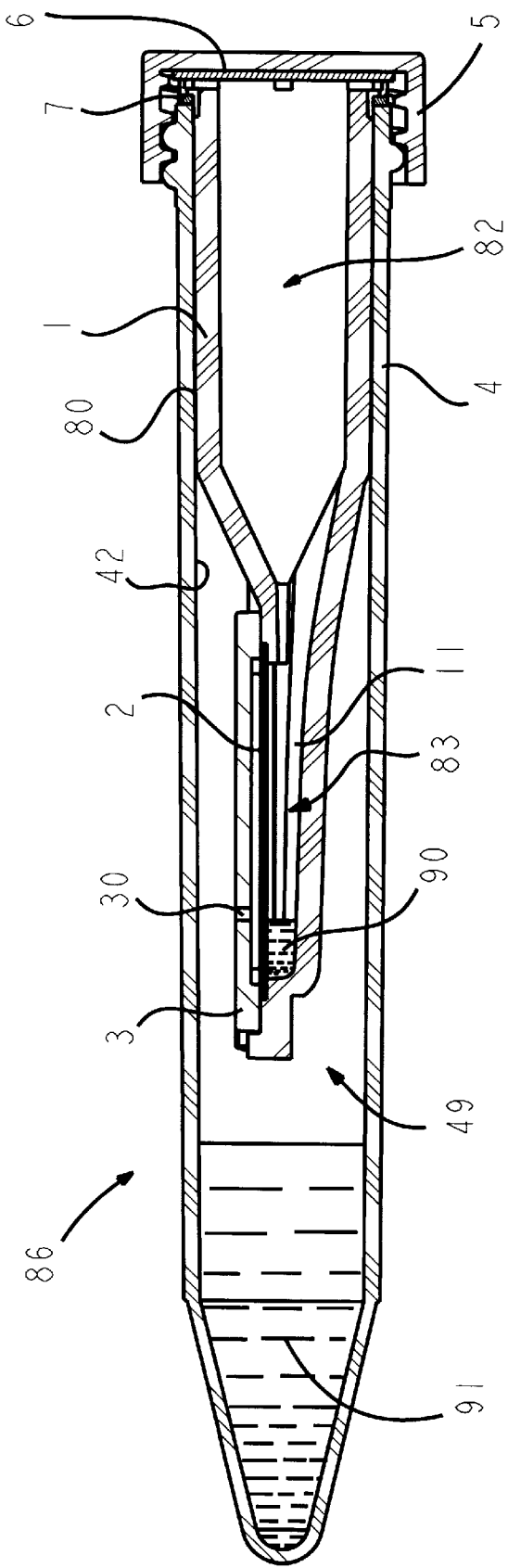
FIG. 17 is a cross-sectional view of the embodiment of the filtration device depicted in FIG. 11, depicting the filtration device in a swinging bucket rotor.

Referring to FIG. 13, FIG. 16b, FIG. 18, and FIG. 22, the concentrate tube assembly 85 is assembled as follows. The outer periphery of filter element 2 is preferably bonded to surface 13 of concentrate tube 1. The filter element bond is preferably a heat seal, but could be a glue seal, a solvent bond or any other type of leak tight seal. The well formed by side walls 61 of concentrate tube 1 facilitates the placement of filter element 2 prior to sealing the filter to surface 13 of concentrate tube 1. In an alternate embodiment, not shown, filter element 2 could be bonded to surface 38 inside energy director 33 of filter cover 3. Surface 34 of filter cover 3 is bonded to surface 22 of concentrate tube 1, preferably using energy director 33 of filter cover 3 and an ultrasonic weld to create bond 48. Bond 48 could however be a glue bond, a solvent bond, a heat bond, or any other leak tight bond. Once concentrate tube 1, chamber 43 will be formed by well 32 of filter cover 3 (defined above), and the downstream surface of filter element 2. Chamber 43 is in fluid flow relationship with the outside atmosphere of filter cover 3 via outlet port 30 of filter cover 3. The user would purchase the concentrate tube assembly 85, assembled. Referring to FIG. 11 and FIG. 17, the concentrate tube assembly may contain flange gasket 7.

The filtration apparatus 86 is assembled by the user, as shown in FIG. 11, FIG. 15, FIG. 17, and FIG. 22 for filtration by inserting the concentrate tube assembly 85 into filtrate tube 4. There is a gap 80 between the outer surface 26 of concentrate tube 1 and the inner surface 42 of filtrate tube 4, because the outer surface 26 of concentrate tube 1 is smaller in diameter than the inner surface 42 of filtrate tube 4. To maximize the liquid capacity of concentrate tube 1 the gap 80 should be made as small as possible. The gap should however, be a minimum of 0.002 inches. The solution to be filtered or concentrated is then placed within the concentrate tube assembly 85. The solution fills the lower chamber 83 of concentrate tube assembly 85, and partially fills the upper chamber 82 of concentrate tube assembly 85. The filtrate tube cap 5 which contains filtrate tube gasket 6 is screwed onto the filtrate tube 4 so that the threads 51 of filtrate tube cap 5 engage the threads 41 of filtrate tube 4. When the filtrate tube cap 5 is secured to filtrate tube 4 the filtrate tube cap gasket 6 will be compressed between the inside surface 52 of filtrate cap 5 and the top of flange 18 of concentrate tube 1, thus sealing the top open end of concentrate tube 1. Likewise concentrate tube rim gasket 7 will be sealed between the bottom of concentrate tube flange 18 and the top rim 89 of filtrate tube 4. Hence the interior of filtrate tube 4, and the interior and exterior of concentrate tube assembly 85 will be sealed, and neither the interior of filtrate tube 4, or the exterior of concentrate tube 1, or the interior of concentrate tube 1 will be in fluid flow relationship, or in air flow relationship with the atmosphere outside of the filtrate tube 4. The assembled device 86 is then inserted into an appropriate centrifuge rotor to perform the filtration. FIG. 17 shows the assembled device 86 oriented 90° from vertical (i.e. in a spinning swinging bucket rotor orientation).

Figure 22:
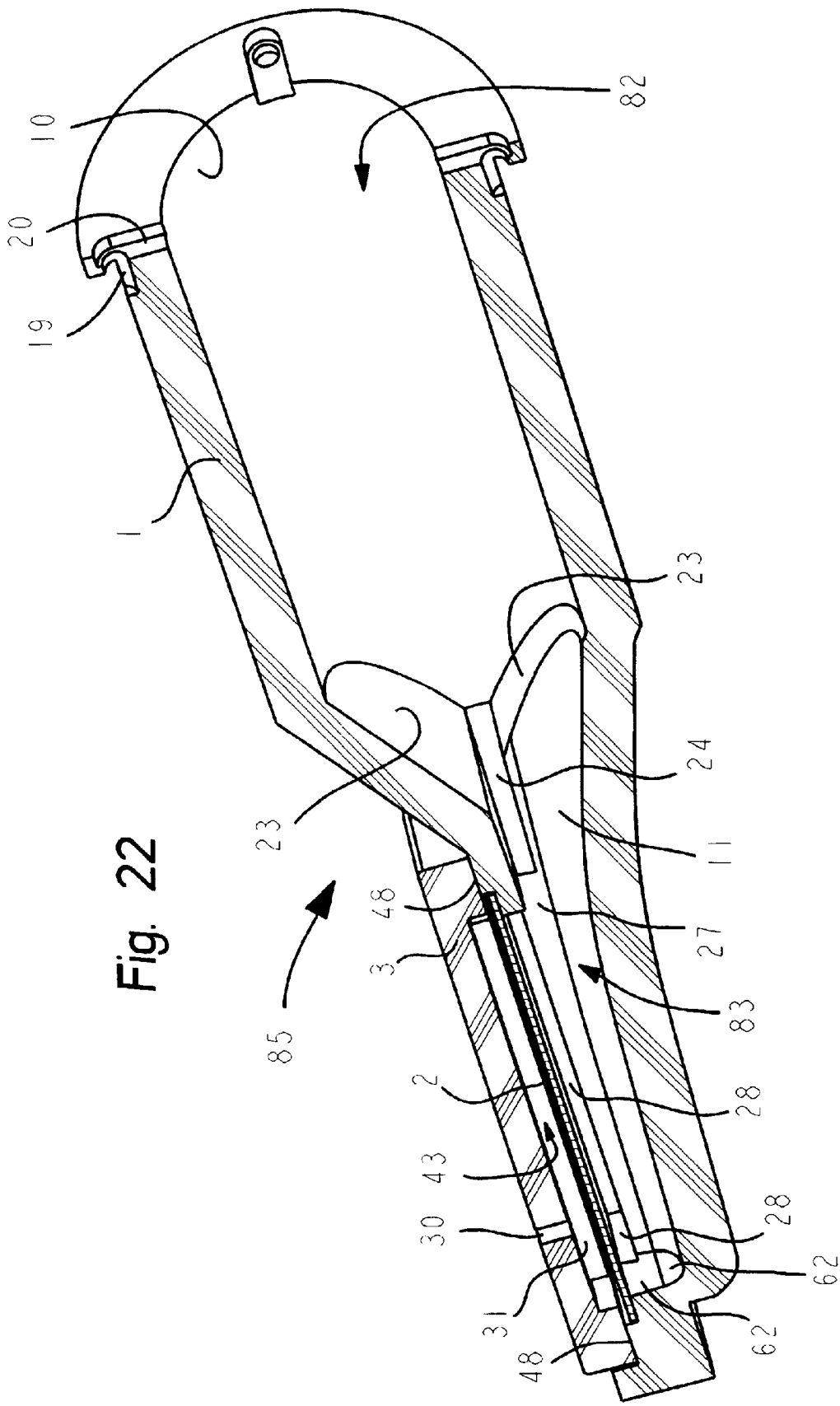
FIG. 22 is an isometric view, having portions thereof removed, of the concentrate tube assembly of the embodiment of the filtration device depicted in FIG. 11.

Referring to FIG. 11, FIG. 17, and FIG. 22 the centrifugal force created by the spinning centrifuge rotor causes the lower molecular weight molecules of concentrate 90 on the upstream side of filter element 2 to flow through filter element 2, into chamber 43. Hence, filtrate that flows through filter element 2 into chamber 43 will accumulate in the bottom of chamber 43, until the filtrate level in chamber 43 reaches outlet port 30 of filter cover 3. At this point any additional filtrate will flow from chamber 43 through outlet port 30 into the interior 49 of filtrate tube 4. Chamber 43 of concentrate tube assembly 85 is in fluid flow relationship with the interior of filtrate tube 4 via outlet port 30 of filter cover 3. Hence, filtrate that flows through filter element 2 into chamber 43 will flow from chamber 43 through outlet port 30 into the interior of filtrate tube 4. The interior of filtrate tube 4 is in air flow relationship with the interior of concentrate tube assembly 85, via the gap 80 between the outer surface 26 of concentrate tube 1 and the inner surface 42 of filtrate tube 4, vent grooves 19 on concentrate tube 1, and vent channels 20 on the top of flange 18 of concentrate tube 1. Therefore as filtrate enters the interior of filtrate tube 4 via port 30 of filter cover 3, the air that is displaced by this filtrate flows through gap 80 between the outside wall of concentrate tube assembly 85 and the inside wall of filtrate tube 4, through grooves 19 of concentrate tube 1, and channels 20 of the top of flange 18 of concentrate tube 1, into the interior of concentrate tube assembly 85 to replace the filtrate that flows from lower chamber 83 of the interior of concentrate tube assembly 85, through filter element 2, into chamber 43, through outlet port 30, into the interior of filtrate tube 4. Hence the pressure in the interior of filtrate tube 4, and the pressure in the interior of concentrate tube assembly 85 remain at atmospheric pressure throughout the filtration process. An additional benefit of securing the concentrate tube assembly 85 to filtrate tube 4, with filtrate tube cap 5 is that if the user accidentally drops the assembled apparatus its contents will not spill.

Alternatively the filtration apparatus 86 may be assembled by the user, as shown in FIG. 11, FIG. 15, FIG. 17, and FIG. 22 for filtration, as described above, without installing concentrate tube rim gasket 7. In this case the interior of filtrate tube 4 will be in air flow relationship with the centrifuge atmosphere via gap 80 between the outer surface 26 of concentrate tube 1 and the inner surface 42 of filtrate tube 4, and via any gap that may exist between the bottom face 88 of the concentrate tube flange and the top edge 89 of filtrate tube 4 because of imperfect mating between these two surfaces, and via the gap between the male threads 41 of filtrate tube 4 and the female thread 51 of filtrate tube cap 5. Hence air that is displaced by filtrate entering filtrate tube 4 may be vented to the centrifuge atmosphere. The interior of the concentrate tube assembly is in air flow relationship with the centrifuge atmosphere via vent channels 20 on the top of flange 18 of concentrate tube 1 and vent grooves 19 on concentrate tube 1, and via the gap between the male threads 41 of filtrate tube 4 and the female threads 51 of filtrate tube cap 5. Hence as the filtrate that flows from lower chamber 83 of the interior of concentrate tube assembly 85, through filter element 2, into chamber 43, through outlet port 30, into the interior of filtrate tube 4, it may be replaced by air from the centrifuge atmosphere. The interior of filtrate tube 4 will also be in air flow relationship with the interior of concentrate tube assembly 85, via the gap 80 between the outer surface 26 of concentrate tube 1 and the inner surface 42 of filtrate tube 4, vent grooves 19 on concentrate tube 1, and vent channels 20 on the top of flange 18 of concentrate tube 1. Therefore as filtrate enters the interior of filtrate tube 4 via port 30 of filter cover 3, the air that is displaced by this filtrate may also flow through grooves 19 of concentrate tube 1, and channels 20 of the top of flange 18 of concentrate tube 1, into the interior of concentrate tube 82 to replace the filtrate that flows from lower chamber 83 of the interior of concentrate tube assembly 85, through filter element 2, into chamber 43, through outlet port 30, into the interior of filtrate tube 4. Hence the pressure in the interior of filtrate tube 4, and the pressure in the interior of concentrate tube assembly 85 remain at atmospheric pressure throughout the filtration process.

Figure 20:
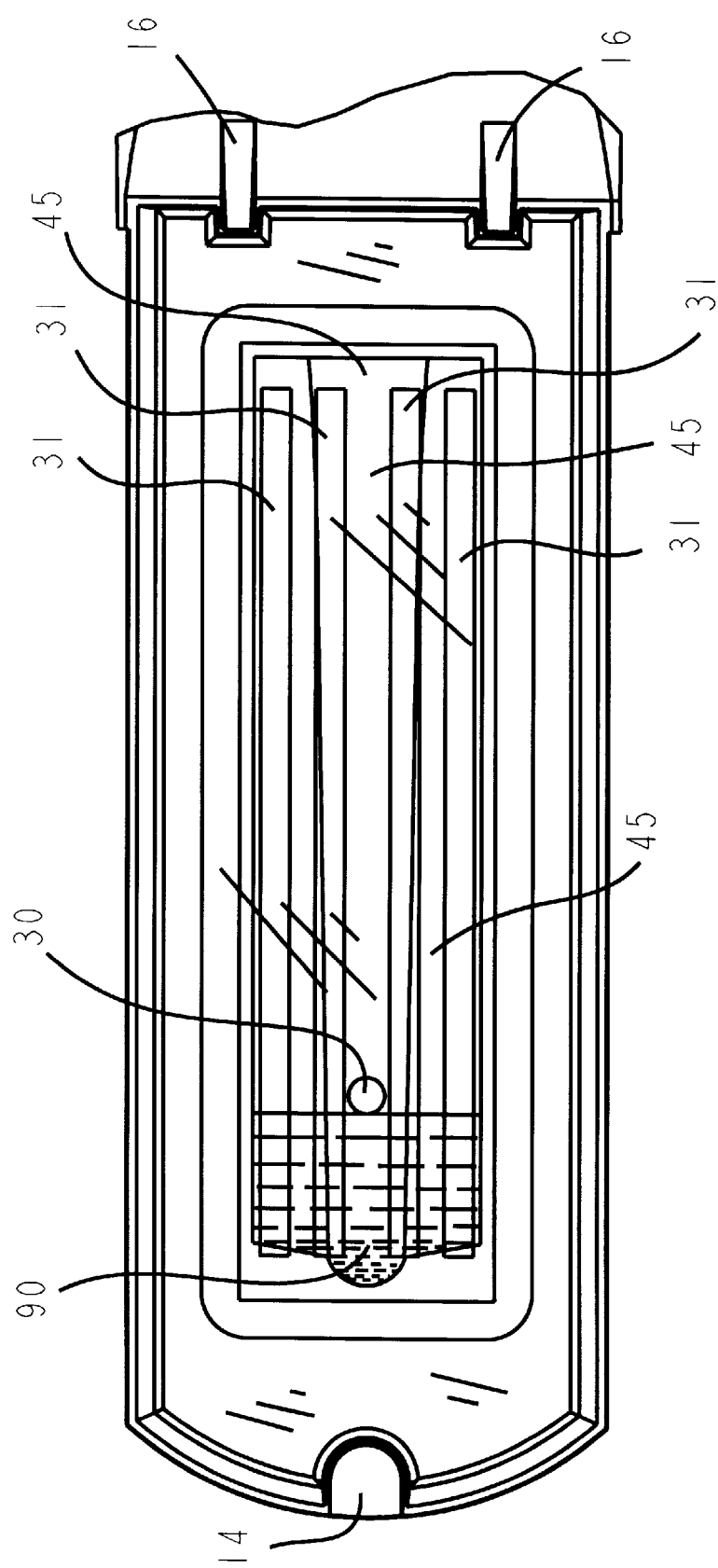
FIG. 20 is a partial top view of a transparent concentrate tube assembly of the embodiment of the filtration device depicted in FIG. 11, showing the retained concentrate in a swinging bucket rotor.
Figure 21:
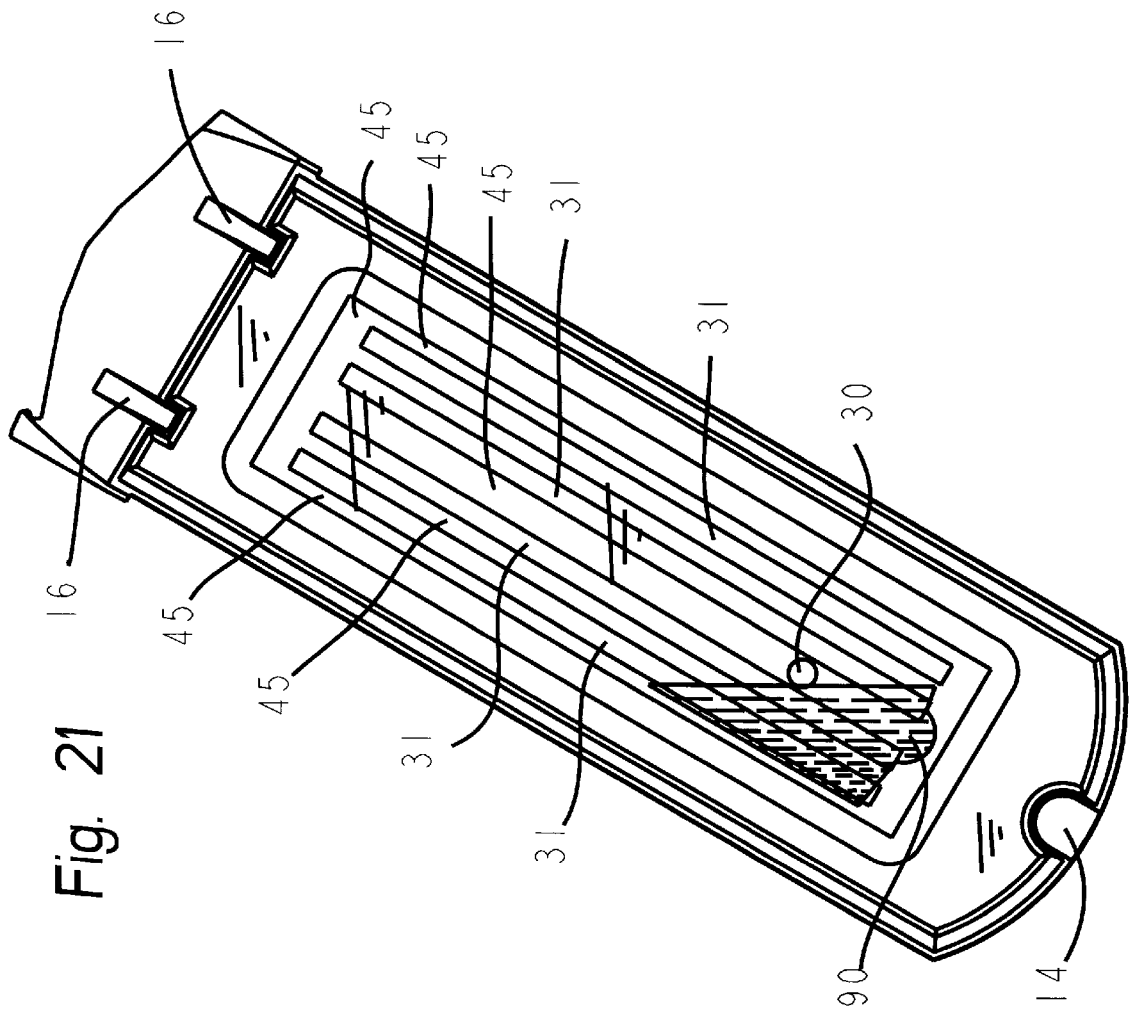
FIG. 21 is a partial top view of a transparent concentrate tube assembly of the embodiment of the filtration device depicted in FIG. 11, showing the retained concentrate in a 30° fixed angle rotor.

The filtration process continues until the liquid level on the concentrate side of filter element 2, and the liquid level on the filtrate side of filter element 2 both reach the outer most edge of outlet port 30 of filter cover 3. The outer most edge of outlet port 30 of filter cover 3 is the edge of outlet port 30 that is the furthest from the axis of rotation of the centrifuge rotor. FIG. 20 shows this level for a swinging bucket centrifuge rotor, and FIG. 21 shows this level for a fixed angle rotor. Once the liquid reaches the level shown in FIG. 21 for a fixed angle rotor, or in FIG. 20 for a swinging bucket rotor, the pressure on the upstream side of filter element 2 will be the same as the pressure on the downstream side of filter element 2, thus liquid flow through filter element 2 will stop. The concentrate that remains on the upstream side of the filter element when filtration is complete is called the retained concentrate volume, or dead stop volume. When device 86 is used in a swinging bucket rotor the dead stop volume will be the same regardless of filter orientation. That is to say the dead stop volume will be the same if filtration device 86 is placed in the swinging bucket centrifuge rotor so that the filter element is oriented parallel to a vertical plane as shown in FIG. 20, or so that the filter element is oriented parallel to a horizontal plane as shown in FIG. 17, or so that the filter element is oriented at any angle relative to either the horizontal or vertical planes. The dead stop volume will be approximately the same for any fixed angle centrifuge rotor angle from 30° to 90° when the filter element is oriented parallel to the vertical plane as shown in FIG. 21.

As long as the upstream side of the lower chamber 83 of concentrate tube assembly 85 is filled with liquid the entire active surface area of filter element 2 will be utilized. Referring to FIG. 23a and FIG. 23b, as the liquid level in lower chamber 83 of concentrate tube assembly 85 falls the portion 87 of the active surface area of filter element 2 that is wet by upstream liquid 90 becomes the usable filter surface area. A substantial portion 87 of the active filter surface continues to be usable filter surface area throughout the entire filtration process. For the embodiment shown in FIGS. 11 through 23b the ratio of (usable surface area)/(concentrate volume) increases from the start of the filtration process until upper chamber 82 of concentrate tube assembly is empty. As lower chamber 83 of concentrate tube assembly goes from full to its dead stop volume the ratio of (usable surface area)/(concentrate volume) will decrease a small amount.

Referring to FIG. 11, FIG. 17, FIG. 19, and FIG. 22 after the filtration process is complete the apparatus 86 can be removed from the centrifuge. The filtrate tube cap 5 with filtrate tube cap gasket 6 can then be removed from apparatus 86, and the remaining concentrate (i.e. the dead stop volume) in lower chamber 83 of concentrate tube assembly 85 can be removed using a pipette tip 95 attached to a pipette mechanism, not shown. The removal of the dead stop volume is facilitated by the pipette channel that is formed by the upper side walls of the pipette channel 27, the bottom pipette channel wall 11, and the end pipette wall 62. After removing the dead stop volume from the concentrate tube assembly with the pipette tip, said dead stop volume can be transferred to a concentrate storage tube such as the concentrate storage tube 170 shown in FIG. 9. The concentrate tube assembly 85, and concentrate tube rim gasket 7 can now be discarded in a safe manner. The filtrate 91 remaining in filtrate tube 4, can be safely stored in filtrate tube 4 by screwing filtrate tube cap 5 with filtrate tube cap gasket 6 back onto filtrate tube 4.

Figure 24:
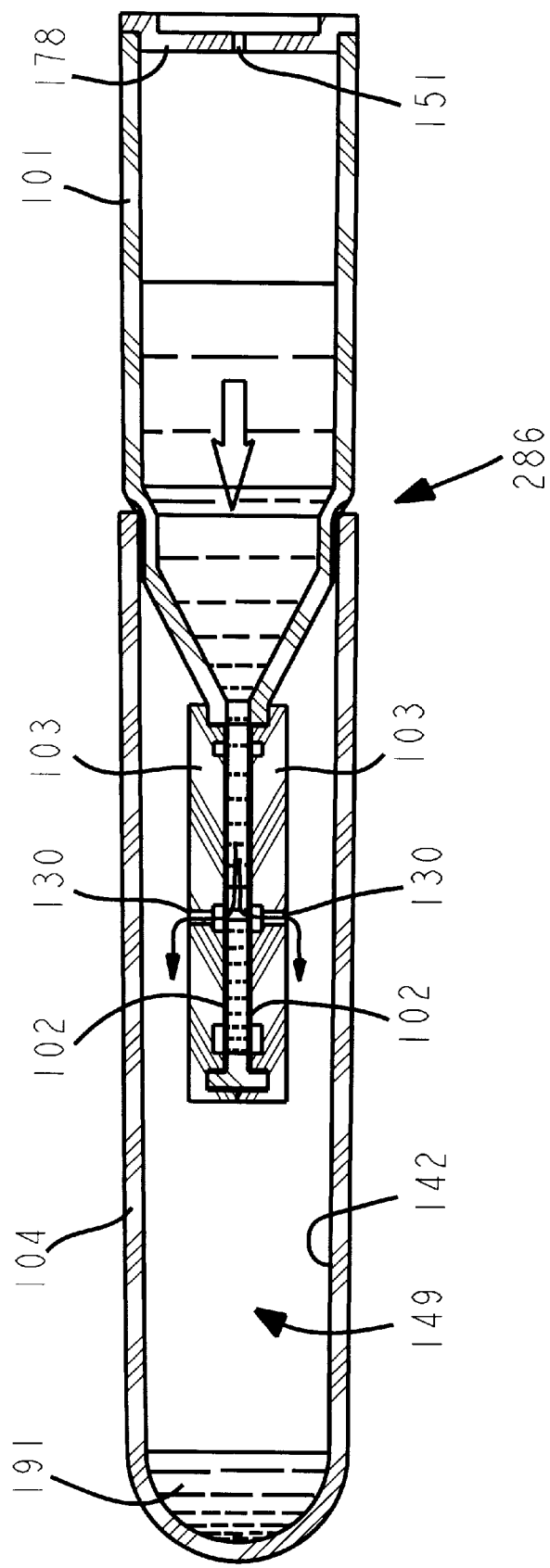
FIG. 24 is a cross-sectional view of the concentrate tube assembly with concentrate tube cap, and the filtrate tube of a second embodiment of the filtration device depicted in FIG. 1.
Figure 25:
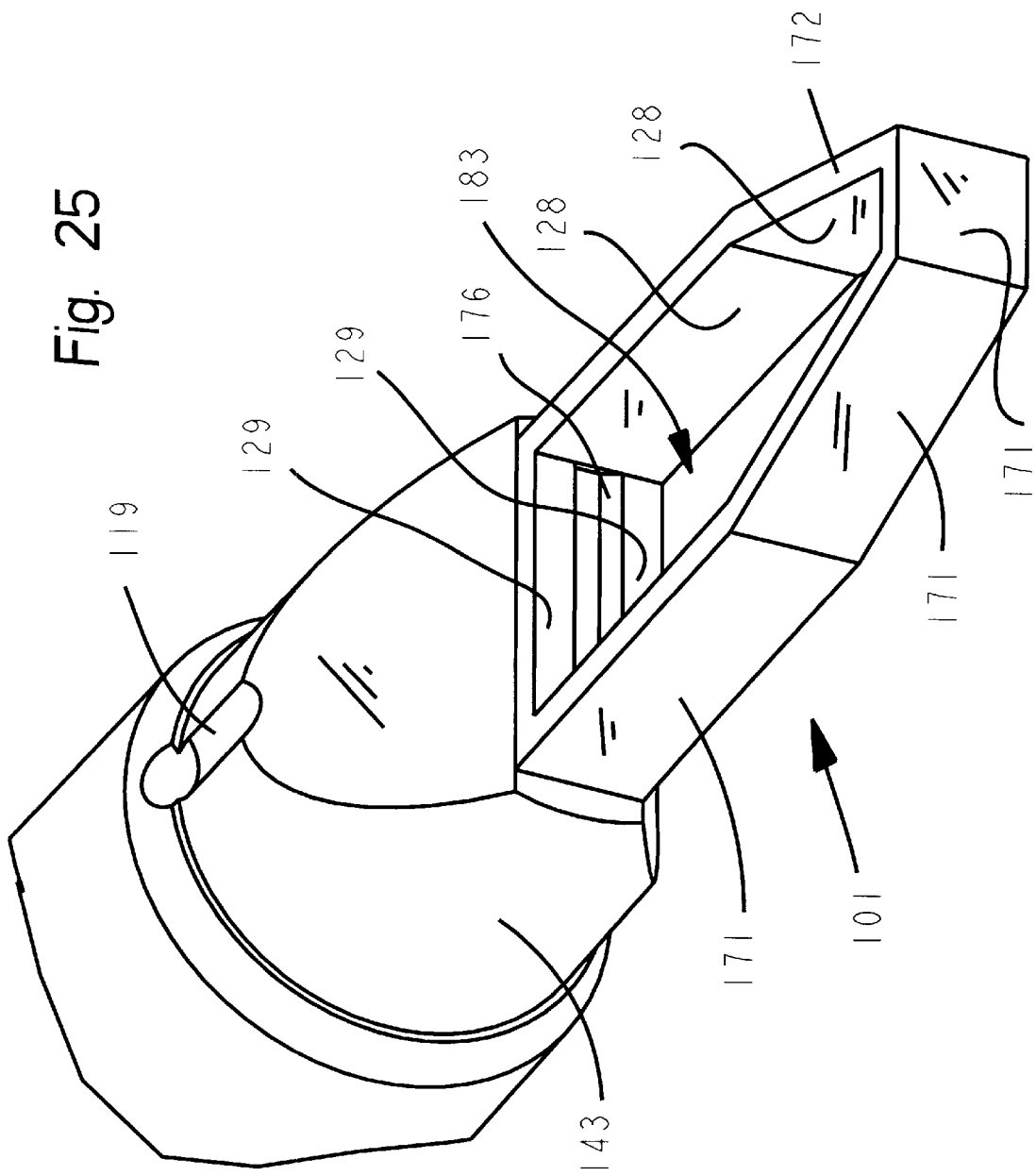
FIG. 25 is a partial isometric view of the lower section of the concentrate tube of a second embodiment of the filtration device depicted in FIG. 1.

An third embodiment of the filtration device constructed in accordance with the principles of the present invention, is shown in FIG. 24 and FIG. 25. Referring to FIG. 2, FIG. 4, FIG. 24, and FIG. 25 the third embodiment is identical to the first embodiment shown in FIG. 2 and FIG. 4 except for the following changes to the concentrate tube assembly. Surface 112 is removed so that well 183 goes completely through the lower portion of concentrate tube 101 (i.e. well 183 is open on its top and bottom sides). Surface 173 is removed so that outside walls 171 extend from the top to the bottom of well 183. A filter cover 103 covers the top of well 183 as in the first embodiment. A second filter cover 103 covers the bottom of well 183. One Filter element 102 is bonded to each filter cover as shown in FIG. 3, and described above.

The apparatus 286 shown in FIG. 24 is assembled for filtration the same as apparatus 186 shown in FIG. 4 is assembled for filtration. The assembly process is described above. The apparatus 286 shown in FIG. 24 functions the same way that the apparatus 186 shown in FIG. 4 functions, with the exception that the apparatus 286 shown in FIG. 24 contains twice the filter element surface area as the apparatus 186 shown in FIG. 4, and the apparatus 286 contains two chambers 138, and two outlet ports 130.

Referring to FIG. 3, and FIG. 24 the centrifugal force created by the spinning centrifuge rotor causes the higher molecular weight molecules of concentrate 190 on the upstream side of filter elements 102 to flow through the two filter elements 102, into filtrate chambers 138 of the two filter covers 103. Chambers 138 of concentrate tube assembly 185 are in fluid flow relationship with the interior of filtrate tube 104 via outlet ports 130 of the two filter covers 103. Hence, filtrate that flows through filter elements 102 into filtrate chambers 138 will accumulate in the bottom into filtrate chambers 138, until the filtrate level in filtrate chambers 138 reaches outlet ports 130 of filter covers 103. At this point any additional filtrate will flow from filtrate chambers 138 through outlet ports 130 into the interior 149 of filtrate tube 104. Vent grooves 119 on concentrate tube 101 allow air in the interior of filtrate tube 104 to be vented into the centrifuge atmosphere, said air being displaced by filtrate 191 in the interior of filtrate tube 104. Vent grooves 119 on concentrate tube 101 prevent pressure buildup in filtrate tube 104 as filtrate tube 104 fills with filtrate. Vent hole 151 on concentrate tube cap 178 allows air to enter the interior of the concentrate tube assembly 185 to replace the filtered liquid, and thus prevent a vacuum buildup in the interior of concentrate tube assembly 185.

The filtration process will continue until the dead stop volume is reached. The dead stop volume for this device will be determined as follows. When the apparatus is used in a swinging bucket rotor both outlet ports 130 will give the same dead stop volume regardless of axial orientation of the apparatus within the centrifuge rotor. When the apparatus is used in a fixed angle rotor and axially aligned so that the filter element is parallel to a vertical plane both outlet ports 130 will give the same dead stop volume. When the apparatus is used in a fixed angle rotor and the axial orientation is such that the filter element is not oriented parallel to a vertical plane, the dead stop volume will be determined by the outlet port 130 of the filter cover that gives the smallest dead stop volume.

The rest of the filtration process for the third embodiment is the same as the process for the first embodiment.

Figure 13:
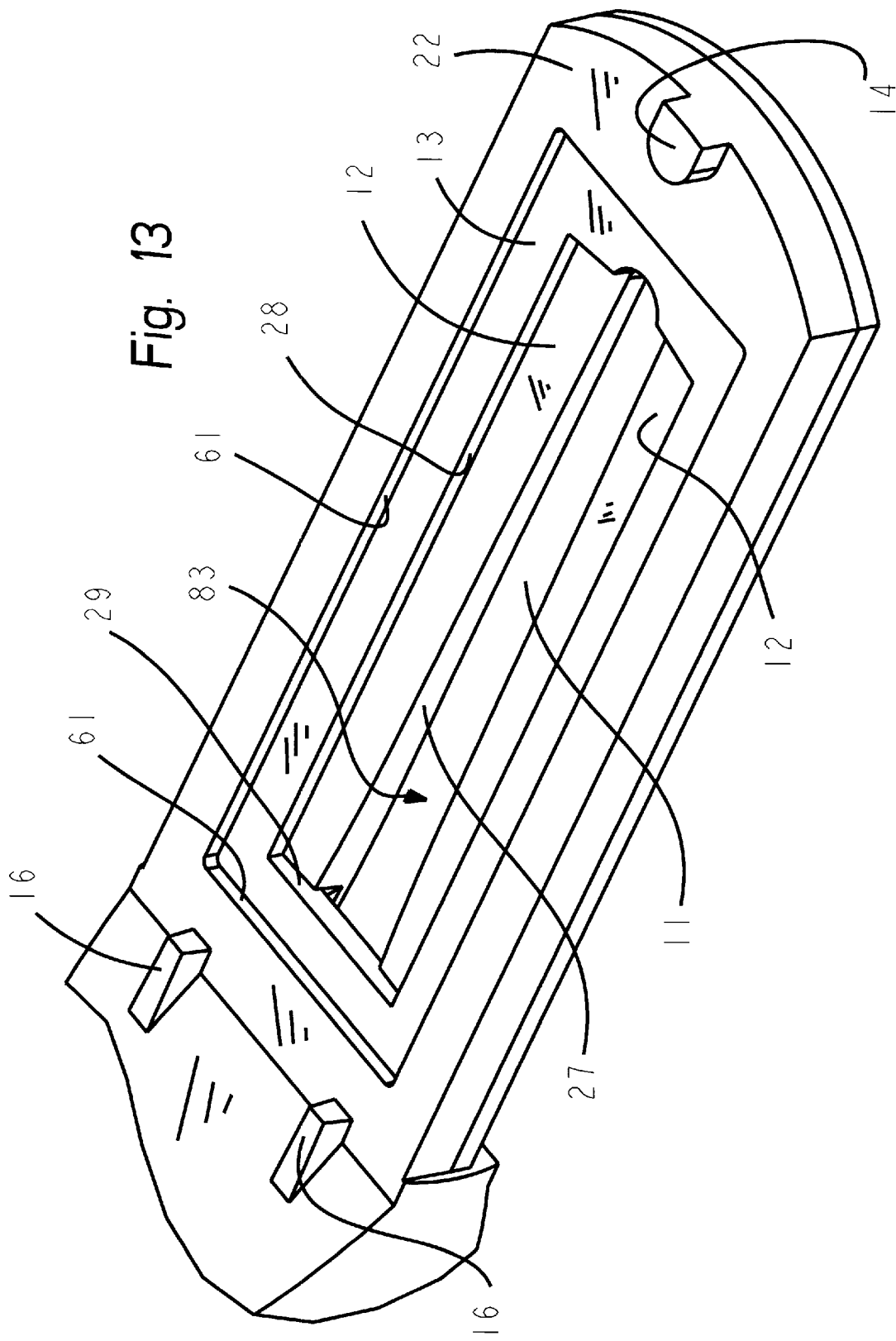
FIG. 13 is a partial isometric view of the concentrate tube of the embodiment of the filtration device depicted in FIG. 11.
Figure 14:
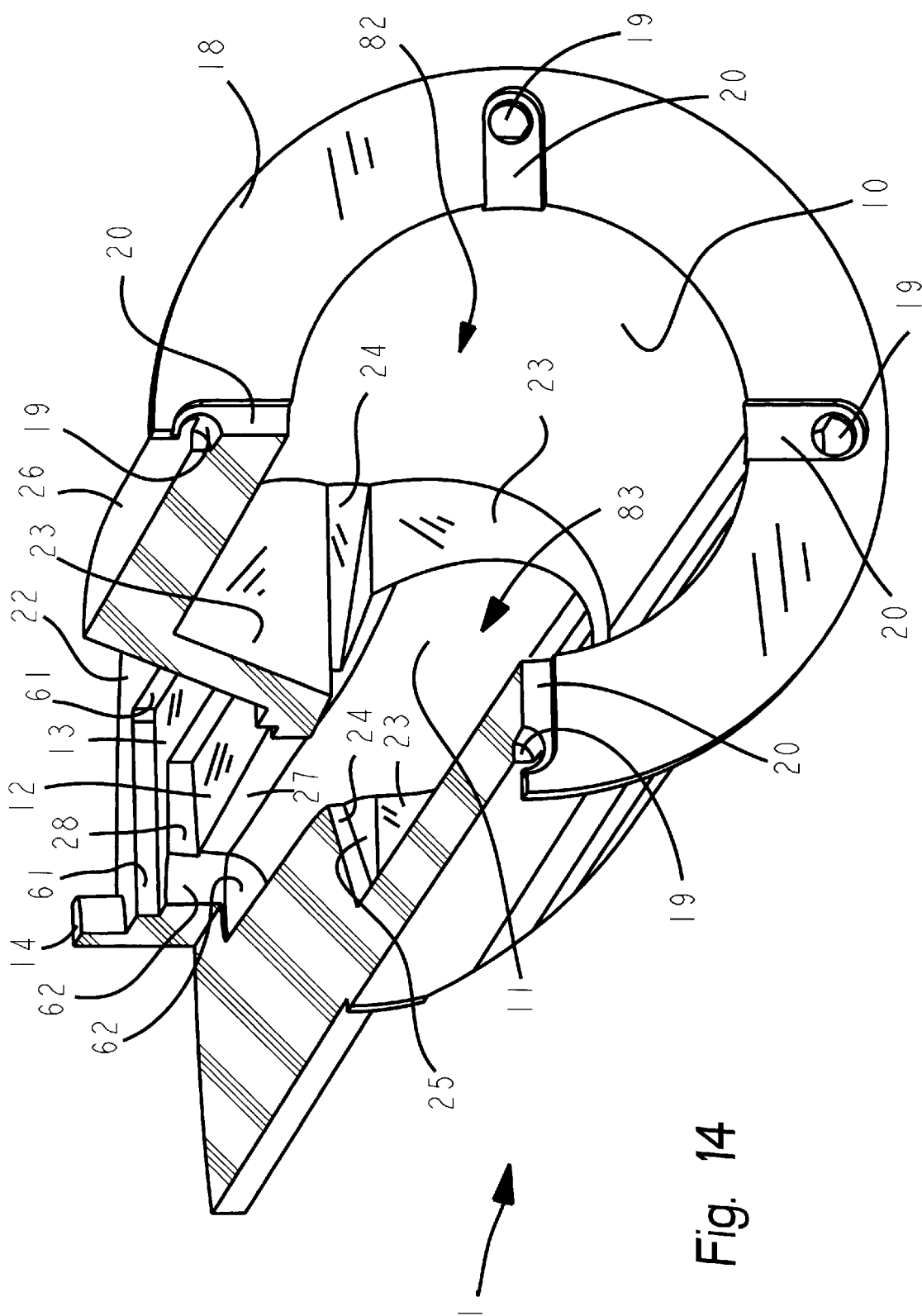
FIG. 14 is an isometric view, having portions thereof removed, of the concentrate tube of the embodiment of the filtration device depicted in FIG. 11.
Figure 18:
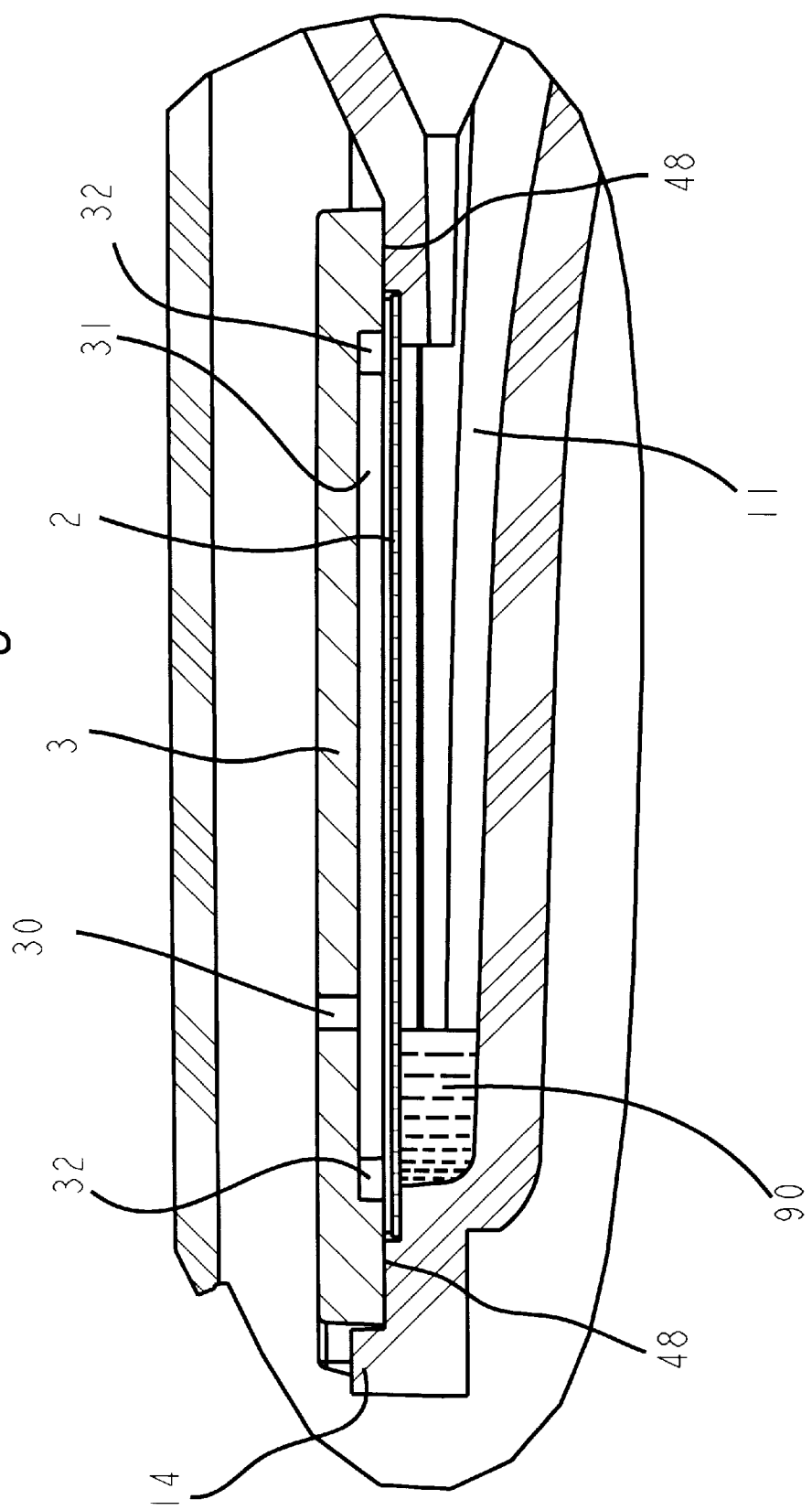
FIG. 18 is a partial cross-sectional view of the concentrate tube assembly of the embodiment of the filtration device depicted in FIG. 11, depicting the filter portion of the concentrate tube assembly.
Figure 19:
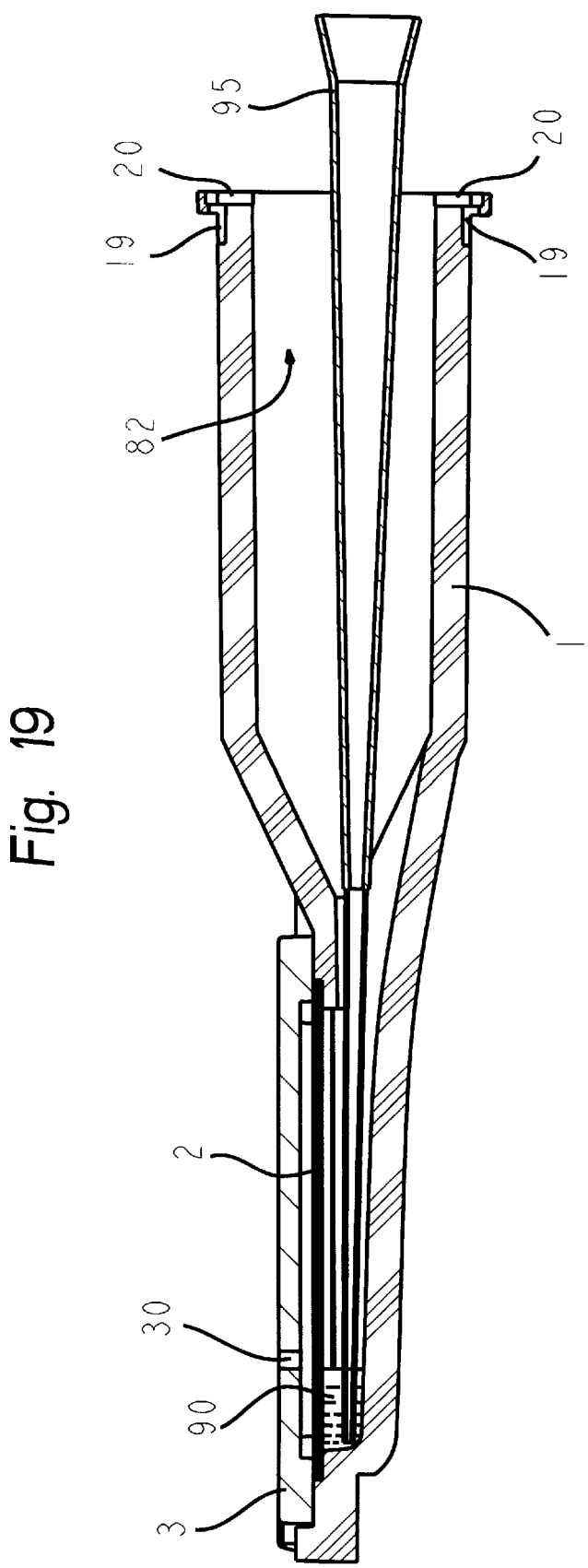
FIG. 19 is a cross-sectional view of the concentrate tube assembly, with a pipette tip, of the embodiment of the filtration device depicted in FIG. 11.

In order to minimize the filtration time (i.e. the time to filter to the dead stop volume), it is necessary to keep the ratio of usable filter surface area to concentrate volume high throughout the filtration process. In addition to using the filter area below the filter cover outlet port, it is also desirable to minimize the volume of the lower part of the concentrate chamber. In the first and third embodiments of the present invention the height of the lower concentrate chamber has to be high enough to allow a pipette tip to reach to the bottom of the lower concentrate chamber to retrieve the dead stop volume. Hence the height of the lower chamber can not be so small as to limit the insertion of a pipette tip. Referring to FIG. 13 and FIG. 18, if the height of side wall 28 is made to small it will not be possible to retrieve all of the dead stop volume because some of this volume will be trapped between surface 12 and the upstream side of the filter element 2 by the capillary action of the small gap between surface 12 and filter 2.

A fourth embodiment of the filtration device constructed in accordance with the principles of the present invention, is shown in FIG. 26, FIG. 27, FIG. 28, FIG. 29, and FIG. 30. This embodiment overcomes the problems described in the previous paragraph. The fourth embodiment includes the following major components: concentrate tube 301, filter element 302, filter cover 303, filter sealing gasket 360, filtrate tube 4, and filtrate tube cap 5. The concentrate tube assembly shown in FIG. 26 fits into a concentrate tube 4, as shown in FIG. 11, and is held in place with a concentrate tube cap 5, also shown in FIG. 11.

Referring to FIG. 26, FIG. 27, FIG. 28, FIG. 29, and FIG. 30 the concentrate tube assembly 385 contains concentrate tube 301, filter element 302, filter cover 303, and filter sealing gasket 360. The concentrate tube assembly 385 contains a concentrate chamber which is divided into a upper chamber 382, a communication chamber 392, and a filtration chamber. The filtration chamber is further divided into the following chambers; a vent chamber 393, a pipette access chamber 394, a dead stop chamber 396, a thin channel chamber 398, and vent channels 397. In the concentrate tube shown in FIGS. 26 through FIG. 29, the pipette access chamber 394 is formed by four sub-chambers 394a, 394b, 394c, and 394d, each chamber being narrower and shorter than the previous one. This design allows a tapered pipette tip to access the dead stop chamber 396, while keeping the volume of the pipette access chamber 394 to a minimum. The pipette access chamber 394 could also be formed as a smooth walled chamber that tapers in and up as it approaches the dead stop chamber 396. The upper concentrate chamber 382 is formed by cylindrical wall 310 and front tapered wall 323. Communication chamber 392 is formed by upper cylindrical wall 369, front tapered wall 324, side cylindrical walls 326, bottom wall 327, and by top wall 325. Vent chamber 393 is formed by front tapered wall 377, side walls 375, side round walls 374, and back wall 372. Dead stop chamber 396 is formed by front walls 366, side walls 365, back walls 363, and sloped bottom walls 364. Filter sealing gasket 360 fits into the well formed by walls 361 of concentrate tube 301 and flat surface 313 of concentrate tube 301. The filter sealing gasket 360 is rectangular in shape, and contains a cutout that is generally rectangular in shape with a V shaped front section. When the filter sealing gasket 360 is placed onto flat surface 313 of concentrate tube 301, the back edge of the gasket cutout aligns with the top edge of back wall 372, the side edges of the gasket cutout align with the top edges of surfaces 375, and the front V shaped edges of the gasket cutout align with the top edges of surfaces 366. Thin channel chamber 398 is formed by the side walls 363 of the filter sealing gasket cutout, the upstream side of filter element 302, and flat surface 313 of the concentrate tube 301. Vent channels 397 communicate between dead stop chamber 396 and vent chamber 393. Tapered wall 323, and tapered wall 324 assure that as filtration occurs all of the liquid in the upper concentrate chamber 382 will flow through communication chamber 392 into vent chamber 393 when the apparatus is used at any rotor angle from 28° to 90°, regardless of the axial orientation of the apparatus in the centrifuge rotor.

Figure 26:
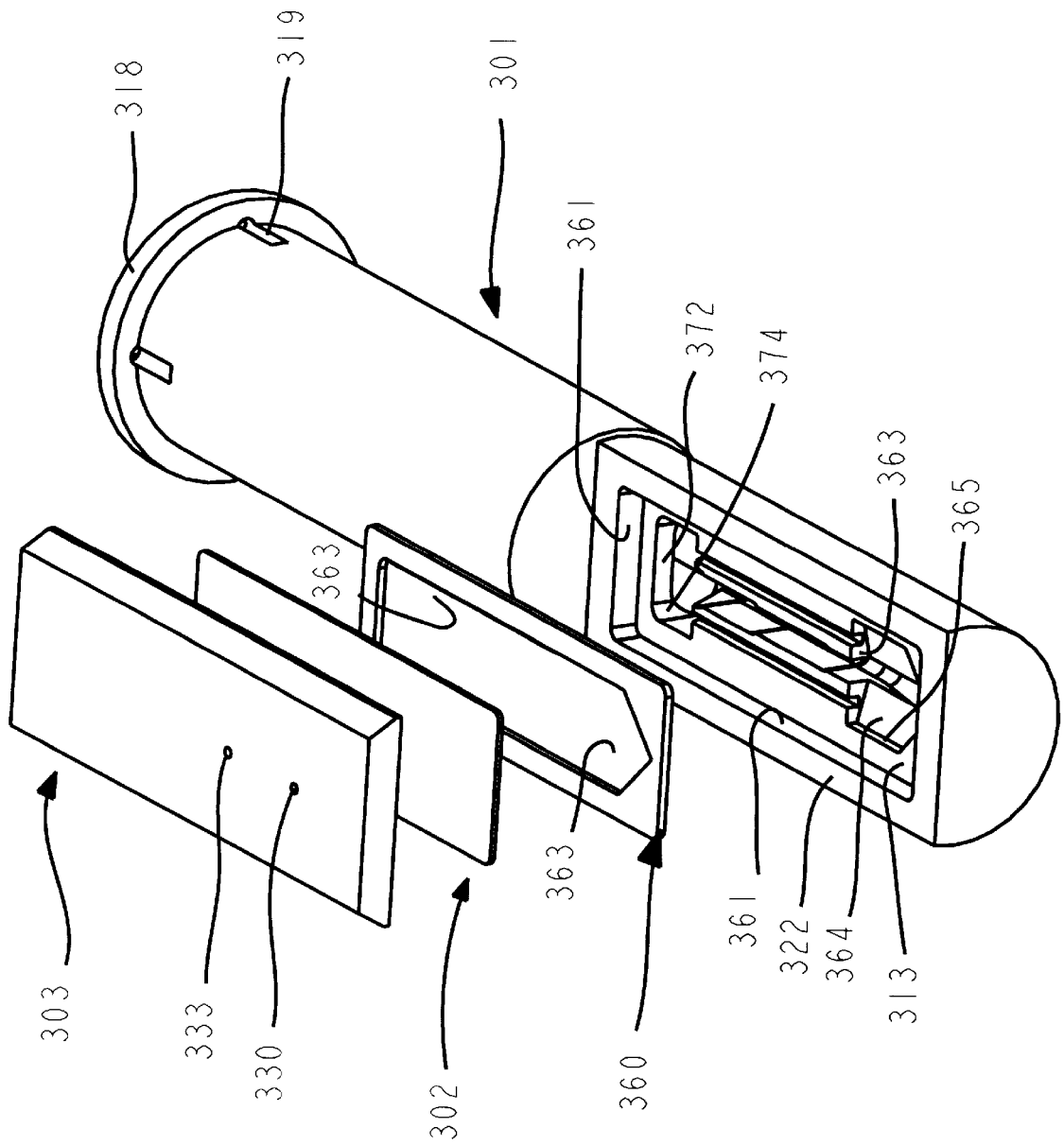
FIG. 26 is an exploded isometric view of the components that make up the concentrate tube assembly of a third embodiment of a filtration apparatus, constructed in accordance with the principles of the present invention, usable within a centrifuge.
Figure 28:
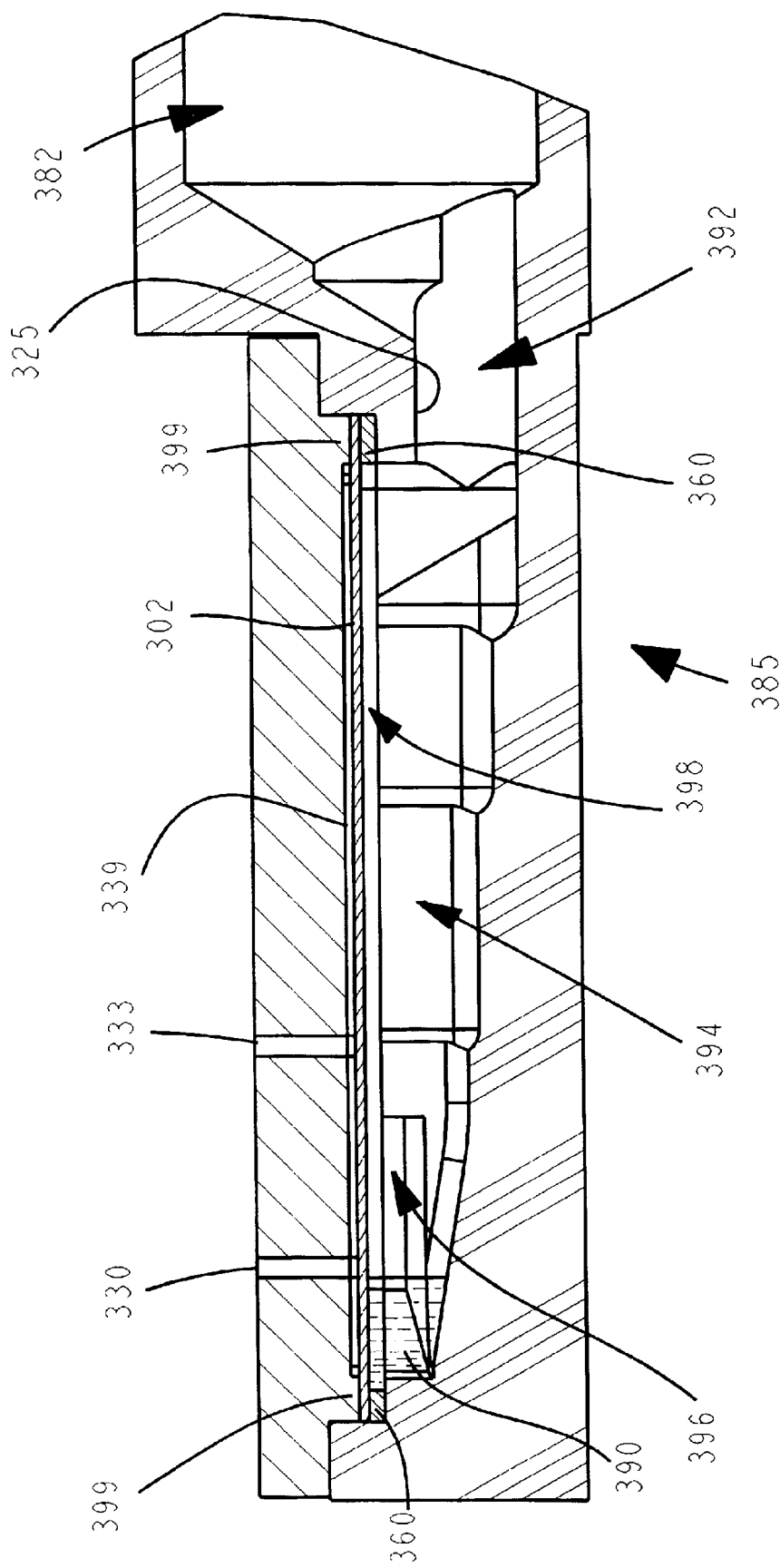
FIG. 28 is a partial cross-sectional view of the concentrate tube assembly of the embodiment of the filtration device depicted in FIG. 26, depicting the filter portion of the concentrate tube assembly.
Figure 30:
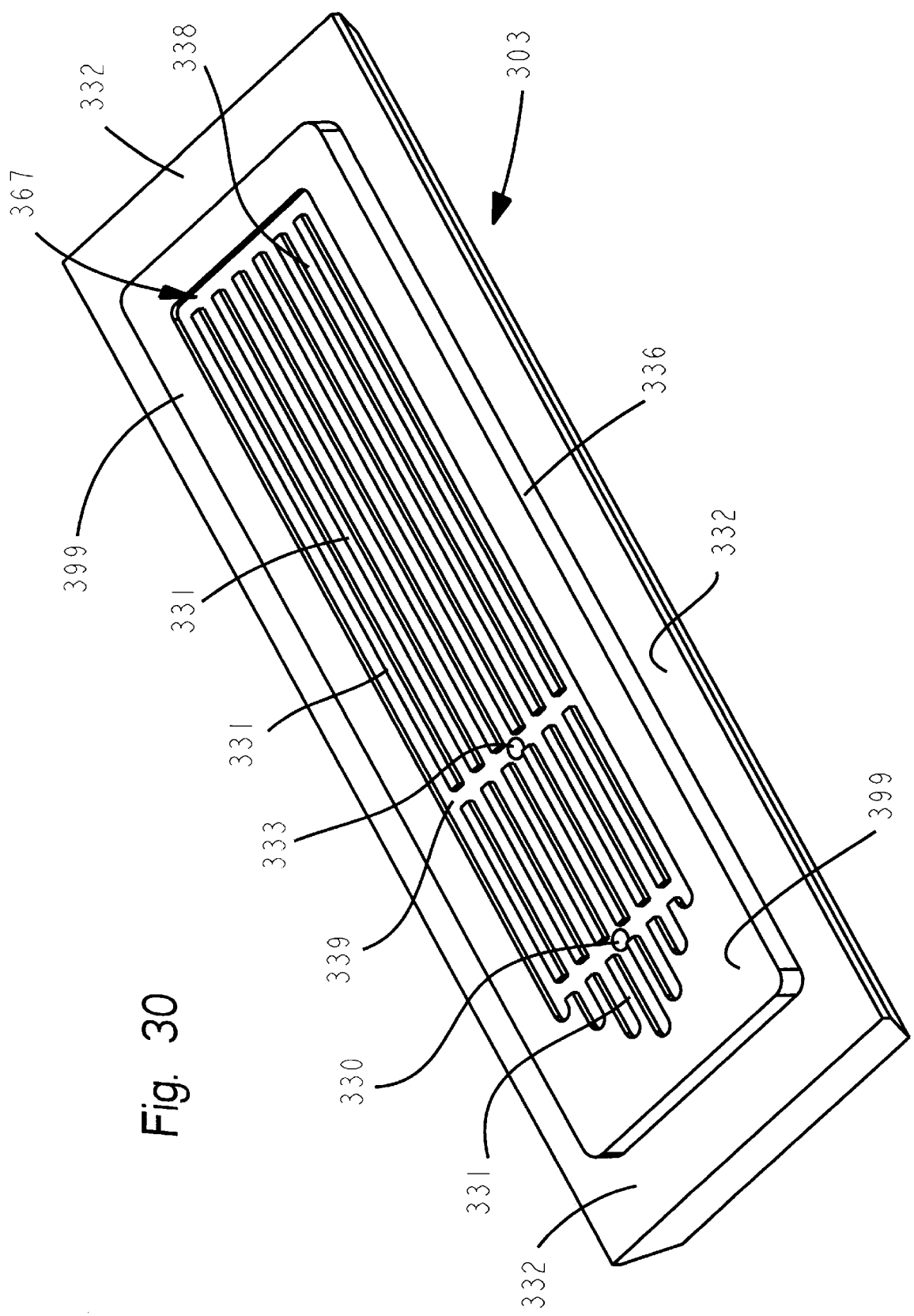
FIG. 30 is a bottom isometric view of the filter cover of the embodiment of the filtration device depicted in FIG. 26.

Referring to FIG. 26, FIG. 28, and FIG. 30, the outer periphery of filter element is preferably sealed between compressed filter sealing gasket 360, and filter sealing rib 399 of filter cover 303. The compressed height of the filter sealing gasket is approximately 0.020", hence the thin channel 398 has a maximum height of 0.020". The filter element could also be sealed to filter sealing rib 399 by a heat seal, ultrasonic seal or glue seal, in which case the filter sealing gasket need not be used.

Referring to FIG. 26 and FIG. 30 the filter cover 303 contains a filter sealing rib 399. The outer periphery of filter sealing rib 399 fits into the well formed by walls 361 of concentrate tube 301, thus providing an alignment means when assembling filter cover 303 to concentrate tube 301. When the filter cover 303 is assembled to the concentrate tube 301, filter sealing rib 399 pushes down on the outer periphery of filter element 302, which in turn compresses the filter sealing gasket 360 between the upstream side of filter element 302 and flat surface 313 of concentrate tube 301, thus creating a leak tight seal around the outer periphery of filter element 302. Filter support ribs 331 protrude from top surface 339. The space in-between and around filter support ribs 331 form channels 338. The volume formed by channels 338 and the downstream side of filter element 302, creates chamber 367. Filter cover 303 also contains outlet port 330, and may contain additional drainage ports 333.

Figure 27:
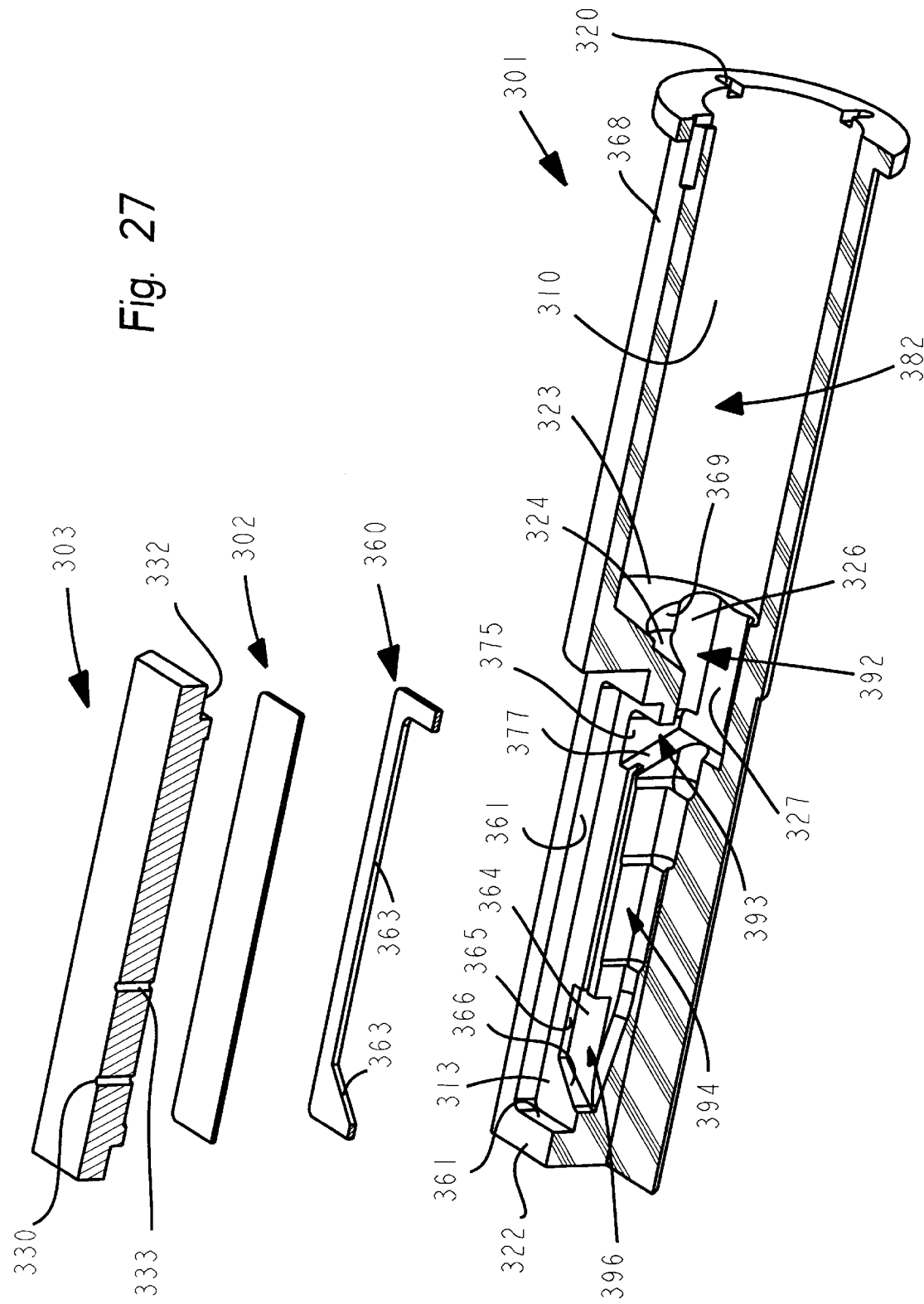
FIG. 27 is an exploded isometric view, having portions thereof removed, of the concentrate tube assembly of the embodiment of the filtration device depicted in FIG. 26.

Referring to FIG. 26, FIG. 27, and FIG. 28, the concentrate tube assembly 385 is assembled as follows. The filter sealing gasket 360 is placed into the well formed by walls 361 of concentrate tube 301, and flat surface 313 of concentrate tube 301. The filter element 302 is placed into the same well on top of filter sealing gasket 360. Filter cover 303 is then assembled to concentrate tube 301, with walls 336 of filter sealing rib 399 of filter cover 303 fitting into the well formed by walls 361 of concentrate tube 301. Surface 332 of filter cover 303 is bonded to surface 322 of concentrate tube 301, preferably with a UV curing glue, but could also be bonded using an ultrasonic weld, a heat bond or any other type of leak tight bond.

The filtration apparatus is assembled by the user, in the same manner as the second embodiment of this invention, as described above. When the user places the solution to be filtered or concentrated into the concentrate tube assembly 385, the solution will flow from the upper chamber 382, through the communication chamber 392, into vent chamber 393, down through the pipette access chamber 394, and fill the dead stop chamber 396. The thin channel chamber 398, and vent channels 397 will then back fill from the dead stop chamber 396 up. Once the filtration chamber is filled with liquid, the liquid level will rise into the upper chamber. A small amount of air may be trapped in the top of vent chamber 393, after the concentrate tube assembly 385 has been filled with solution. This air can be dislodged by gently tapping the concentrate tube assembly 385, or this small amount of air will automatically be forced either through the filter, or into the upper chamber 382, by centrifugal force once the centrifuge begins to spin.

Referring to FIG. 26, FIG. 27, and FIG. 28 the centrifugal force created by the spinning centrifuge rotor causes the lower molecular weight molecules of concentrate 390 on the upstream side of filter element 302 to flow through filter element 302, into chamber 367. Hence, filtrate that flows through filter element 302 into chamber 367 will accumulate in the bottom chamber 367, until the filtrate level in chamber 367 reaches outlet port 330 of filter cover 303. Chamber 367 of concentrate tube assembly 385 is in fluid flow relationship with the interior of filtrate tube 4 via outlet port 330 of filter cover 303. Additional outlet ports such as port 333 may be added to filter cover 303 above outlet port 330, to assure that there will not be any pressure buildup on the downstream side of filter element 302 above outlet port 330. Hence, filtrate that flows through filter element 302 into chamber 367 will flow from chamber 367 through outlet port 330 into the interior of filtrate tube 4. The interior of filtrate tube 4 is in air flow relationship with the interior of concentrate tube assembly 385, via the gap 80 between the outer surface 368 of concentrate tube 301 and the inner surface 42 of filtrate tube 4, vent grooves 319 on concentrate tube 301, and vent channels 320 on the top of flange 318 of concentrate tube 301. Therefore as filtrate enters the interior of filtrate tube 4 via port 330 of filter cover 303, the air that is displaced by this filtrate flows through gap 80 between the outside wall of concentrate tube assembly 385 and the inside wall of filtrate tube 4, through grooves 319 of concentrate tube 301, and channels 320 of the top of flange 318 of concentrate tube 301, into the interior of concentrate tube assembly 385 to replace the filtrate that flows from the filtration chamber of the interior of concentrate tube assembly 385, through filter element 302, into chamber 367, through outlet port 330, into the interior of filtrate tube 4. Hence the pressure in the interior of filtrate tube 4, and the pressure in the interior of concentrate tube assembly 385 remain at atmospheric pressure throughout the filtration process. An additional benefit of securing the concentrate tube assembly 385 to filtrate tube 4, with filtrate tube cap 5 is that if the user accidentally drops the assembled apparatus its contents will not spill.

Figure 29:
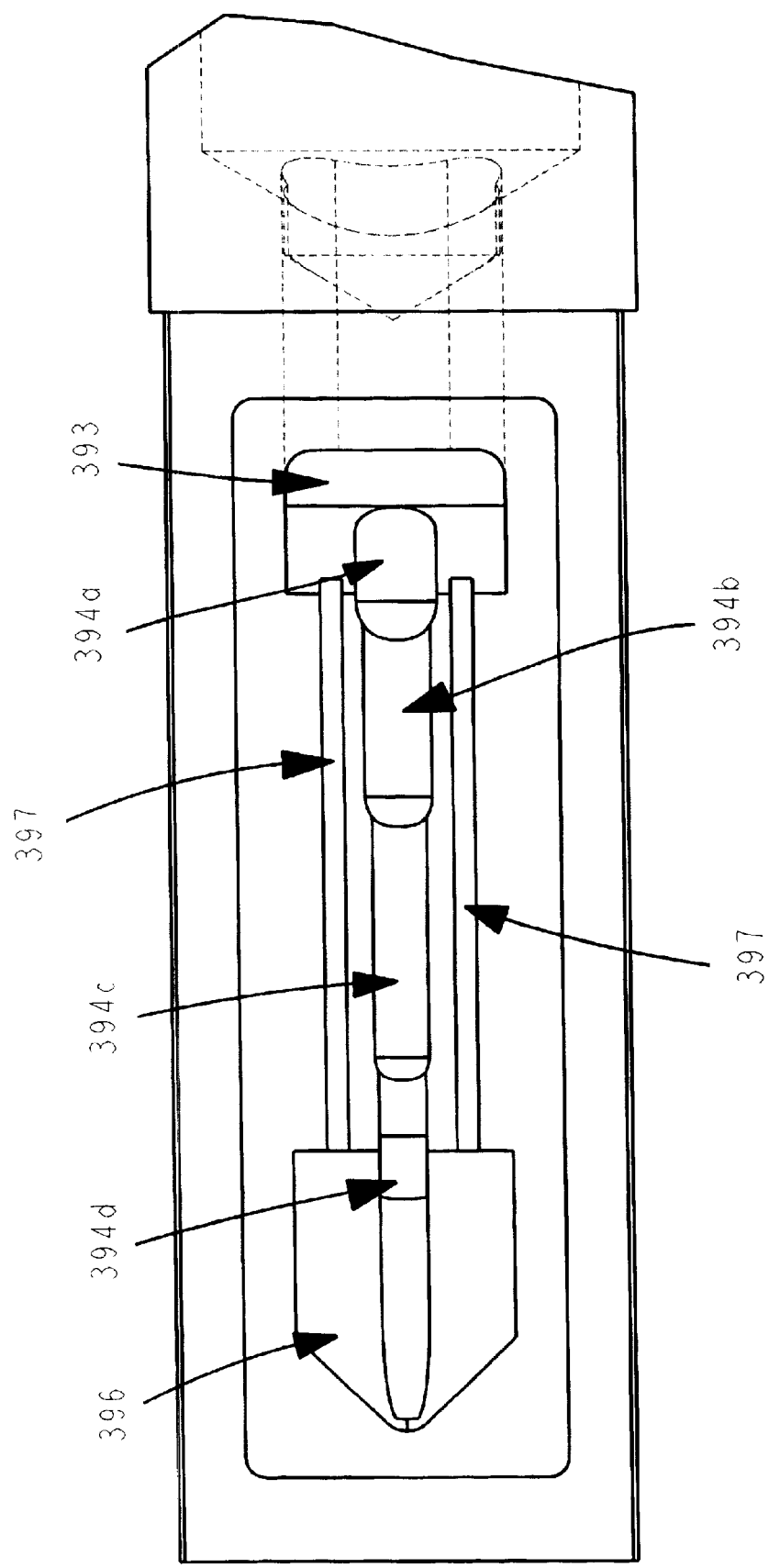
FIG. 29 is a partial top view of the concentrate tube of the embodiment of the filtration device depicted in FIG. 26, depicting the filter portion of the concentrate tube.

The filtration process continues until the liquid level on the concentrate side of filter element 302, and the liquid level on the filtrate side of filter element 302 both reach the outer most edge of outlet port 330 of filter cover 303. The outer most edge of outlet port 330 of filter cover 303 is the edge of outlet port 330 that is the furthest from the axis of rotation of the centrifuge rotor. FIG. 28 shows this level for a swinging bucket centrifuge rotor. The level for a fixed angle rotor is similar to that shown in FIG. 7. Once the liquid reaches the level shown in FIG. 7 for a fixed angle rotor, or in FIG. 28 for a swinging bucket rotor, the pressure on the upstream side of filter element 302 will be the same as the pressure on the downstream side of filter element 302, thus liquid flow through filter element 302 will stop. The concentrate that remains on the upstream side of the filter element when filtration is complete is called the retained concentrate volume, or dead stop volume. When device 386 is used in a swinging bucket rotor the dead stop volume will be the same regardless of filter orientation. That is to say the dead stop volume will be the same if filtration device 386 is placed in the swinging bucket centrifuge rotor so that the filter element is oriented parallel to a vertical plane as shown in FIG. 29, or so that the filter element is oriented parallel to a horizontal plane as shown in FIG. 28, or so that the filter element is oriented at any angle relative to either the horizontal or vertical planes. The dead stop volume will be approximately the same for any fixed angle centrifuge rotor angle from 30° to 90° when the filter element is oriented parallel to the vertical plane the same as the orientation shown in FIG. 21.

As long as the upstream side of the filtration chamber of concentrate tube assembly 385 is filled with liquid the entire active surface area of filter element 302 will be utilized. If the pipette access chamber 394 is made just large enough to accommodate a small pipette tip (i.e. a gel loading tip for example), and if the volume of the vent chamber 393 is made just large enough to give the proper venting, and if the dead stop chamber 396 is made just high enough to allow easy and complete removal of the dead stop volume, and if the vent channels 397 are made just large enough to allow easy and complete removal of the dead stop volume, then the volume of the filtration chamber will be minimized. For example, a concentrate tube assembly 385 with a maximum volume capacity of 4 ml, and an active filter surface area of approximately 2 $cm^2$, will have a filtration chamber with a total volume of approximately 250 $\mu$l.

After the filtration process is complete the apparatus can be removed from the centrifuge. The filtrate tube cap 5 with filtrate tube cap gasket 6 can then be removed from the filtrate tube 4, and the remaining concentrate (i.e. the dead stop volume) in dead stop chamber 396 of concentrate tube assembly 385 can be removed using a pipette tip attached to a pipette mechanism. After filtration is complete the filter element 302 will be wetted. The wetted filter will swell, and may droop down to flat surface 313 of concentrate tube 301, because the height of the thin channel chamber is 0.020" or less. When the gel loading pipette tip is inserted into the device to remove the dead stop volume it will pass through communication chamber 392, and then go through pipette access chamber 394, and then into dead stop chamber 396. The communication chamber 392 is below the filter element 302, and the pipette access chamber 394 tapers inward, and upward as it approaches the dead stop chamber 396. This geometry prevents the pipette tip from scratching against the filter element 302, and causes the end of the gel loading tip to bend up to access the end of the dead stop chamber 396. Although the pipette access chamber 394 can be a snug fit for the pipette tip, the communication chamber 392 is the full width of vent chamber 393. The volume of the dead stop chamber 396 should be larger than the dead stop volume, so that there will be an air space above the dead stop volume when the filtration is complete. When filtration is complete, dead stop chamber 396 is in air flow relationship with upper chamber 382 through, vent channels 397, vent chamber 393, and through communication chamber 392. The height of the dead stop chamber 396 is greater than the height of the thin channel chamber 398, hence as the pipette tip removes liquid from the dead stop chamber 396 an equal volume of air can enter the dead stop chamber 396, through vent channels 397, vent chamber 393, and communication chamber 392. This venting allows easy and complete removal of the dead stop volume by the pipette tip. After removing the dead stop volume from the concentrate tube assembly with the pipette tip, said dead stop volume can be transferred to a concentrate storage tube such as the concentrate storage tube 170 shown in FIG. 9. The concentrate tube assembly 385, and concentrate tube rim gasket 7 can now be discarded in a safe manner. The filtrate 91 remaining in filtrate tube 4, can be safely stored in filtrate tube 4 by screwing filtrate tube cap 5 with filtrate tube cap gasket 6 back onto filtrate tube 4.

What is claimed:

1. A centrifugal liquid filtration apparatus for separating filtrate and concentrate from a solution capable of being used in a fixed angle or swinging bucket centrifuge rotor comprising:
    (a) a concentrate tube assembly capable of containing a solution therein, comprising;
        (i) a concentrate tube,
        (ii) a micro-porous filter element,
        (iii) a filter cover,
        (iv) a concentrate tube cap, and
        (v) a filtrate tube for collecting filtrate;
    (b) said concentrate tube assembly containing a first chamber capable of containing unfiltered liquid therein, said first chamber being divided into an upper part and a lower part;
    (c) a second chamber capable of collecting filtered liquid therein, said second chamber being in fluid flow relationship with the lower part of the first chamber;
    (d) a means for filtering liquid within the first chamber prior to flowing into the second chamber; and (e) a port leading from the second chamber into the interior of said filtrate tube, said port being disposed a sufficient distance above the bottom of the second chamber whereby the lower part of said first chamber is prevented from filtering to dryness.

2. A filtration apparatus of claim 1 wherein the bottom portion of said upper part of said first chamber is shaped so that all liquid in said upper part of said first chamber will flow into the said lower part of said first chamber, for any centrifuge rotor angle from 28° to 90°, and for any axial orientation of the filtration apparatus within the centrifuge rotor.

3. A filtration apparatus of claim 2 wherein a lower portion of said concentrate tube assembly is inserted into said filtrate tube.

4. A filtration apparatus of claim 3 wherein said filtrate tube engages said concentrate tube assembly with an interference fit.

5. A filtration apparatus of claim 4 wherein the means for preventing said first chamber from filtering to dryness is the location of the port leading from the second chamber to the interior of said filtrate tube.

6. A filtration apparatus of claim 5 wherein the volume of concentrate remaining in the lower part of said first chamber after filtration is complete, is independent of the axial orientation of said filtration apparatus in the centrifuge rotor when used within a swinging bucket rotor.

7. A filtration apparatus of claim 5 wherein the volume of concentrate remaining in the lower part of said first chamber after filtration is complete, will not vary more than 10% when the apparatus is used at any rotor angle from 28° to 90°, and when said apparatus is oriented axially within said rotor so that said filter element is oriented parallel to a vertical plane.

8. A filtration apparatus of claim 5 further comprising a vented cap for covering the upper portion of the concentrate tube assembly and allowing said apparatus to be spun in a centrifuge.

9. A filtration apparatus of claim 5 further comprising a venting means for venting said filtrate tube.

10. A filtration apparatus of claim 9 wherein the venting means for venting said filtrate tube is one or more grooves in said concentrate tube.

11. A filtration apparatus of claim 1 wherein said microporous filter element is sealed to said filter cover.

12. A filtration apparatus of claim 11 wherein said means for filtering liquid within the first chamber prior to flowing into the second chamber, is said micro-porous filter element.

13. A centrifugal liquid filtration apparatus for separating filtrate and concentrate from a solution capable of being used in a fixed angle or swinging bucket centrifuge rotor comprising:
(a) a concentrate tube assembly capable of containing a solution therein, comprising:
(i) a concentrate tube,
(ii) a micro-porous filter element, and
(iii) a filter cover,
(b) a filtrate tube for collecting filtrate;
(c) a filtrate tube cap;
(d) a filtrate tube cap gasket;
(e) said concentrate tube assembly containing a first chamber capable of containing unfiltered liquid therein, said first chamber being divided into an upper part and a lower part;
(f) a second chamber capable of collecting filtered liquid therein, said second chamber being in fluid flow relationship with the lower part of the first chamber;
(g) a means for filtering liquid within the first chamber prior to flowing into the second chamber; and
(h) a port leading from the second chamber into the interior of said filtrate tube, said port being disposed a sufficient distance above the bottom of the second chamber whereby the lower part of said first chamber is prevented from filtering to dryness.

14. A filtration apparatus of claim 13 wherein the bottom portion of said upper part of said first chamber is shaped so that all liquid in said upper part of said first chamber will flow into the said lower part of said first chamber, for any centrifuge rotor angle from 28° to 90°, and for any axial orientation of the filtration apparatus within the centrifuge rotor.

15. A filtration apparatus of claim 14 wherein said concentrate tube assembly is inserted into said filtrate tube.

16. A filtration apparatus of claim 15 wherein a flange on the upper portion of said concentrate tube positions said concentrate tube assembly within said filtrate tube.

17. A filtration apparatus of claim 16 wherein said concentrate tube flange contains one or more ports that communicate between the top and bottom faces of said flange.

18. A filtration apparatus of claim 17 wherein the top face of said concentrate tube flange contains one or more grooves that communicate between said flange ports and the interior of said concentrate tube assembly, the number of grooves being equal to the number of flange ports.

19. A filtration apparatus of claim 18 wherein there is a gap between the outer wall of said concentrate tube assembly, and the inner wall of said filtrate tube.

20. A filtration apparatus of claim 19 wherein the filtrate tube cap is threadedly engagable to the filtrate tube.

21. A filtration apparatus of claim 20 wherein the filtrate tube cap gasket seals the opening at the top of the concentrate tube when the concentrate tube cap is threadably engaged to the filtrate tube.

22. A filtration apparatus of claim 21 wherein there is a concentrate tube gasket between the bottom face of said flange on the upper portion of said concentrate tube, and the top edge of said filtrate tube.

23. A filtration apparatus of claim 22 wherein the concentrate tube gasket seals any gap that may exist between the bottom face of said concentrate tube flange and the top edge of said filtrate tube when the concentrate tube cap is threadably engaged to the filtrate tube.

24. A filtration apparatus of claim 23 wherein air in said filtrate tube that is displaced by filtrate entering said filtrate tube is vented through said gap between the outer wall of said concentrate tube assembly, and the inner wall of said filtrate tube, and through said one or more ports that communicate between the top and bottom faces of said flange, and through said one or more grooves that communicate between said flange ports and the interior of said concentrate tube assembly, into the interior of said concentrate tube assembly.

25. A filtration apparatus of claim 21 wherein air in said filtrate tube that is displaced by filtrate entering said filtrate tube is vented through said gap between the outer wall of said concentrate tube assembly, and the inner wall of said filtrate tube, and through any gap that may exist between the bottom face of said concentrate tube flange and the top edge of said filtrate tube when the concentrate tube cap is threadably engaged to the filtrate tube, and through the gap between the threads of said filtrate tube and the threads of said filtrate tube cap, to atmosphere; and wherein atmospheric air can enter the interior of said concentrate tube assembly to replace filtrate that passes through said filter element into said second chamber, through the gap between the threads of said filtrate tube and the threads of said filtrate tube cap, and through said one or more ports that communicate between the top and bottom faces of said flange, and through said one or more grooves that communicate between said flange ports and the interior of said concentrate tube assembly.

26. A filtration apparatus of claim 13 wherein said micro-porous filter element is sealed to an open face of the bottom portion of said concentrate tube.

27. A filtration apparatus of claim 13 wherein said micro-porous filter element is sealed to said filter cover.

28. A filtration apparatus of claim 13 wherein the means for preventing said first chamber from filtering to dryness is the location of the port leading from the second chamber to the interior of said filtrate tube.

29. A centrifugal liquid filtration apparatus for separating filtrate and concentrate from a solution capable of being used in a fixed angle or swinging bucket centrifuge rotor comprising:
   (a) a concentrate tube assembly capable of containing a solution therein, comprising:
      (i) a concentrate tube,
      (ii) two micro-porous filter elements, and
      (iii) two filter covers,
   (b) said concentrate tube assembly containing a first chamber capable of containing unfiltered liquid therein, said first chamber being divided into an upper part and a lower part;
   (c) a second chamber capable of collecting filtered liquid therein, said second chamber being in fluid flow relationship with the lower part of the first chamber;
   (d) a third chamber capable of collecting filtered liquid therein, said third chamber being in fluid flow relationship with the lower part of the first chamber;
   (e) a means for filtering liquid within the first chamber prior to flowing into the second and third chambers; and
   (f) a first port leading from the second chamber into the interior of said filtrate tube;
   (g) a second port leading from the third chamber into the interior of said filtrate tube said first and second ports being disposed a sufficient distance above the bottom of the second chamber and the third chambers respectively whereby the lower part of said first chamber is prevented from filtering to dryness.

30. A filtration apparatus of claim 29 wherein the bottom portion of said upper part of said first chamber is shaped so that all liquid in said upper part of said first chamber will flow into said lower part of said first chamber, for any centrifuge rotor angle from 28° to 90°, and for any axial orientation of the filtration apparatus within the centrifuge rotor.

31. A filtration apparatus of claim 30 wherein a lower portion of said concentrate tube assembly is inserted into said filtrate tube.

32. A filtration apparatus of claim 31 wherein said filtrate tube engages said concentrate tube assembly with an interference fit.

33. A filtration apparatus of claim 32 wherein the means for preventing said first chamber from filtering to dryness is the location of the port leading from the second chamber to the interior of said filtrate tube, or the location of the port leading from the third chamber to the interior of said filtrate tube.

34. A filtration apparatus of claim 33 wherein the volume of concentrate remaining in the lower part of said first chamber after filtration is complete, is independent of the axial orientation of said filtration apparatus in the centrifuge rotor when used within a swinging bucket rotor.

35. A filtration apparatus of claim 33 wherein the volume of concentrate remaining in the lower part of said first chamber after filtration is complete, will not vary more than 10% when the apparatus is used at any rotor angle from 28° to 90°, and when said apparatus is oriented axially within said rotor so that said filter element is oriented parallel to a vertical plane.

36. A filtration apparatus of claim 33 further comprising a vented cap for covering the upper portion of the concentrate tube assembly and allowing said apparatus to be spun in a centrifuge.

37. A filtration apparatus of claim 36 further comprising a venting means for venting said filtrate tube.

38. A filtration apparatus of claim 37 wherein the venting means for venting said filtrate tube is one or more grooves in said concentrate tube.

39. A filtration apparatus of claim 29 wherein said micro-porous filter elements are sealed to said filter covers.

40. A filtration apparatus of claim 39 wherein said means for filtering liquid within the first chamber prior to flowing into the second chamber, are said micro-porous filter elements.

41. A centrifugal liquid filtration apparatus for separating filtrate and concentrate from a solution capable of being used in a fixed angle or swinging bucket centrifuge rotor comprising:
   (a) a concentrate tube assembly capable of containing a solution therein, comprising:
      (i) a concentrate tube,
      (ii) a micro-porous filter element,
      (iii) a filter cover, and
      (iv) a filter sealing gasket
   (b) a filtrate tube for collecting filtrate;
   (c) a filtrate tube cap;
   (d) a filtrate tube cap gasket;
   (e) said concentrate tube assembly containing a first chamber capable of containing unfiltered liquid therein, said first chamber being divided into an upper part, a central part, and a lower part;
   (f) said upper part and said lower part being connected by said central part;
   (h) said lower part comprising:
      (i) a vent chamber;
      (ii) a pipette access chamber;
      (iii) at least one vent channel;
      (iv) a dead stop chamber; and
      (v) a thin channel member;
   (h) a second chamber capable of collecting filtered liquid therein, said second chamber being in fluid flow relationship with the lower part of the first chamber;
   (i) a means for filtering liquid within the first chamber prior to flowing into the second chamber; and
   (j) a port leading from the second chamber into the interior of said filtrate tube, said port being disposed a sufficient distance above the bottom of the second chamber whereby the lower part of said first chamber is prevented from filtering to dryness.

42. A filtration apparatus of claim 41 wherein the bottom portion of said upper part of said first chamber is shaped so that all liquid in said upper part of said first chamber will flow into the said central part, and then into said lower part of said first chamber, for any centrifuge rotor angle from 28° to 90°, and for any axial orientation of the filtration apparatus within the centrifuge rotor.

43. A filtration apparatus of claim 42 wherein said concentrate tube assembly is inserted into said filtrate tube.

44. A filtration apparatus of claim 43 wherein a flange on the upper portion of said concentrate tube positions said concentrate tube assembly within said filtrate tube.

45. A filtration apparatus of claim 44 wherein said concentrate tube flange contains one or more ports that communicate between the top and bottom faces of said flange.

46. A filtration apparatus of claim 45 wherein the top face of said concentrate tube flange contains one or more grooves that communicate between said flange ports and the interior of said concentrate tube assembly, the number of grooves being equal to the number of flange ports.

47. A filtration apparatus of claim 46 wherein there is a gap between the outer wall of said concentrate tube assembly, and the inner wall of said filtrate tube.

48. A filtration apparatus of claim 47 wherein the filtrate tube cap is threadedly engagable to the filtrate tube.

49. A filtration apparatus of claim 48 wherein the filtrate tube cap gasket seals the opening at the top of the concentrate tube when the concentrate tube cap is threadably engaged to the filtrate tube.

50. A filtration apparatus of claim 49 wherein there is a concentrate tube gasket between the bottom face of said flange on the upper portion of said concentrate tube, and the top edge of said filtrate tube.

51. A filtration apparatus of claim 50 wherein the concentrate tube gasket seals any gap that may exist between the bottom face of said concentrate tube flange and the top edge of said filtrate tube when the concentrate tube cap is threadably engaged to the filtrate tube.

52. A filtration apparatus of claim 51 wherein air in said filtrate tube that is displaced by filtrate entering said filtrate tube is vented through said gap between the outer wall of said concentrate tube assembly, and the inner wall of said filtrate tube, and through said one or more ports that communicate between the top and bottom faces of said flange, and through said one or more grooves that communicate between said flange ports and the interior of said concentrate tube assembly, into the interior of said concentrate tube assembly.

53. A filtration apparatus of claim 49 wherein air in said filtrate tube that is displaced by filtrate entering said filtrate tube is vented through said gap between the outer wall of said concentrate tube assembly, and the inner wall of said filtrate tube, and through any gap that may exist between the bottom face of said concentrate tube flange and the top edge of said filtrate tube when the concentrate tube cap is threadably engaged to the filtrate tube, and through the gap between the threads of said filtrate tube and the threads of said filtrate tube cap, to atmosphere; and wherein atmospheric air can enter the interior of said concentrate tube assembly to replace filtrate that passes through said filter element into said second chamber, through the gap between the threads of said filtrate tube and the threads of said filtrate tube cap, and through said one or more ports that communicate between the top and bottom faces of said flange, and through said one or more grooves that communicate between said flange ports and the interior of said concentrate tube assembly.

54. A filtration apparatus of claim 41 wherein said microporous filter element is sealed between a peripheral rib of said filter cover and said filter sealing gasket, said seal forming a leak tight seal on the gasket side of the seal.

55. A filtration apparatus of claim 54 wherein said filter sealing gasket seals said lower chamber of said concentrate tube assembly, thus preventing leakage from said first chamber to said second chamber.

56. A filtration apparatus of claim 41 wherein said microporous filter element is sealed to said filter cover.

57. A filtration apparatus of claim 41 wherein the means for preventing said first chamber from filtering to dryness is the location of the port leading from the second chamber to the interior of said filtrate tube.

58. A filtration apparatus of claim 41 wherein the height of said thin channel chamber is less than 0.050 inches.

59. A filtration apparatus of claim 41 wherein the height of said dead stop chamber is greater than the height of said thin channel chamber.

60. A filtration apparatus of claim 41 wherein said pipette access channel is made small enough so that only a gel loading pipette tip can slide through said pipette access chamber to the bottom of said dead stop chamber.

61. A filtration apparatus of claim 60 wherein said pipette access channel is positioned so that said gel loading pipette tip can not scratch the surface of the filter element.

62. A filtration apparatus of claim 41 wherein the volume of the filtration chamber is less than 300 µl.

63. A filtration apparatus of claim 41 wherein the filter cover contains more than one outlet port.

* * * * *